United States Patent
Gomes et al.

(10) Patent No.: US 12,121,677 B2
(45) Date of Patent: Oct. 22, 2024

(54) DEVICES AND METHODS TO PREVENT INADVERTENT MOTION OF DYNAMICALLY RIGIDIZING APPARATUSES

(71) Applicant: NEPTUNE MEDICAL INC., Burlingame, CA (US)

(72) Inventors: Garrett J. Gomes, Pleasant Hill, CA (US); Alexander Q. Tilson, Burlingame, CA (US); Charles Steele Love, Santa Barbara, CA (US); Mark C. Scheeff, Oakland, CA (US); William J. Evans, San Francisco, CA (US)

(73) Assignee: Neptune Medical Inc., Burlingame, CA (US)

( * ) Notice: Subject to any disclaimer, the term of this patent is extended or adjusted under 35 U.S.C. 154(b) by 0 days.

(21) Appl. No.: 18/263,517

(22) PCT Filed: Jan. 31, 2022

(86) PCT No.: PCT/US2022/014497
§ 371 (c)(1),
(2) Date: Jul. 28, 2023

(87) PCT Pub. No.: WO2022/165302
PCT Pub. Date: Aug. 4, 2022

(65) Prior Publication Data
US 2024/0033484 A1     Feb. 1, 2024

Related U.S. Application Data

(60) Provisional application No. 63/143,739, filed on Jan. 29, 2021.

(51) Int. Cl.
*A61M 25/01*     (2006.01)
*A61M 25/00*     (2006.01)
(Continued)

(52) U.S. Cl.
CPC .... *A61M 25/0155* (2013.01); *A61M 25/0045* (2013.01); *A61M 25/0136* (2013.01);
(Continued)

(58) Field of Classification Search
CPC ............ A61B 1/00078; A61B 1/00071; A61B 1/00082; A61B 1/00135; A61B 5/065;
(Continued)

(56) References Cited

U.S. PATENT DOCUMENTS 2,268,321 A     12/1941  Flynn
2,767,705 A     10/1956  Moore
(Continued)

FOREIGN PATENT DOCUMENTS

AU     2013207571 B2     8/2013
CN        2613655 Y      4/2004
(Continued)

OTHER PUBLICATIONS

Dow, Dow white paper: Can you estimate modulus from durometer hardness for silicones: Yes, but you only roughly and you must choose your modulus carefully!; 5 pages; retrieved from the internet (https://www.dow.com/content/dam/doc/documents/en-us/tech-art/11/11/37/11-3716-01-durometer-hardness-for-silicones.pdf) on Jan. 18, 2023.

(Continued)

*Primary Examiner* — Scott J Medway
*Assistant Examiner* — Anh Bui
(74) *Attorney, Agent, or Firm* — Shay Glenn LLP

(57) ABSTRACT

Described herein are rigidizing apparatuses (e.g., rigidizing apparatuses, and systems including one or more rigidizing apparatus, including, but not limited to overtubes) that are configured to prevent harm or damage to a patient when rigidized.

14 Claims, 10 Drawing Sheets

(51) Int. Cl.
*A61M 25/06* (2006.01)
*A61M 39/22* (2006.01)

(52) U.S. Cl.
CPC .............. *A61M 2025/0681* (2013.01); *A61M 2039/226* (2013.01); *A61M 2205/18* (2013.01); *A61M 2205/332* (2013.01); *A61M 2205/3331* (2013.01); *A61M 2205/581* (2013.01); *A61M 2205/583* (2013.01)

(58) Field of Classification Search
CPC .. A61M 2025/0915; A61M 2025/0063; A61M 2025/015; A61M 2025/0079; A61M 2025/0076; A61M 2025/0197; A61M 25/0012; A61M 25/0052; A61M 25/0133; A61M 25/0136
See application file for complete search history.

(56) References Cited

U.S. PATENT DOCUMENTS

| | | |
|---|---|---|
| 3,859,986 A | 1/1975 | Okada et al. |
| 3,998,216 A | 12/1976 | Hosono |
| 4,066,071 A | 1/1978 | Nagel |
| 4,141,364 A | 2/1979 | Schultze |
| 4,151,800 A | 5/1979 | Dotts et al. |
| 4,176,662 A | 12/1979 | Frazer |
| 4,425,919 A | 1/1984 | Alston, Jr. |
| 4,551,140 A | 11/1985 | Shinohara |
| 4,690,131 A | 9/1987 | Lyddy, Jr. et al. |
| 4,696,544 A | 9/1987 | Costella |
| 4,717,379 A | 1/1988 | Ekholmer |
| 4,794,412 A | 12/1988 | Casey et al. |
| 4,794,912 A | 1/1989 | Lia |
| 4,815,450 A | 3/1989 | Patel |
| 4,817,613 A | 4/1989 | Jaraczewski et al. |
| 4,893,613 A | 1/1990 | Hake |
| 4,913,369 A | 4/1990 | Lia et al. |
| 4,959,058 A | 9/1990 | Michelson |
| 4,961,738 A | 10/1990 | Mackin |
| 4,967,732 A | 11/1990 | Inoue |
| 5,018,436 A | 5/1991 | Evangelista et al. |
| 5,019,121 A | 5/1991 | Krauter |
| 5,037,386 A | 8/1991 | Marcus et al. |
| 5,050,585 A | 9/1991 | Takahashi |
| 5,105,819 A | 4/1992 | Wollschlager et al. |
| 5,123,421 A | 6/1992 | Sinofsky |
| 5,125,143 A | 6/1992 | Takahashi |
| 5,174,276 A | 12/1992 | Crockard |
| 5,188,595 A | 2/1993 | Jacobi |
| 5,201,908 A | 4/1993 | Jones |
| 5,251,611 A | 10/1993 | Zehel et al. |
| 5,337,733 A | 8/1994 | Bauerfeind et al. |
| 5,360,440 A | 11/1994 | Andersen |
| 5,496,292 A | 3/1996 | Burnham |
| 5,531,685 A | 7/1996 | Hemmer et al. |
| 5,531,719 A | 7/1996 | Takahashi |
| 5,577,992 A | 11/1996 | Chiba et al. |
| 5,601,588 A | 2/1997 | Tonomura et al. |
| 5,603,991 A | 2/1997 | Kupiecki et al. |
| 5,607,435 A | 3/1997 | Sachdeva et al. |
| 5,624,381 A | 4/1997 | Kieturakis |
| 5,632,734 A | 5/1997 | Galel et al. |
| 5,662,587 A | 9/1997 | Grundfest et al. |
| 5,662,621 A | 9/1997 | Lafontaine |
| 5,746,692 A | 5/1998 | Bacich et al. |
| 5,749,828 A | 5/1998 | Solomon et al. |
| 5,759,151 A | 6/1998 | Sturges |
| 5,779,624 A | 7/1998 | Chang |
| 5,782,811 A | 7/1998 | Samson et al. |
| 5,823,961 A | 10/1998 | Fields et al. |
| 5,882,347 A | 3/1999 | Mouris Laan et al. |
| 5,891,112 A | 4/1999 | Samson |
| 5,891,114 A | 4/1999 | Chin et al. |
| 5,906,591 A | 5/1999 | Dario et al. |
| 5,916,145 A | 6/1999 | Chu et al. |
| 5,916,147 A | 6/1999 | Boury |
| 5,951,539 A | 9/1999 | Nita et al. |
| 5,976,074 A | 11/1999 | Moriyama |
| 6,090,099 A | 7/2000 | Samson et al. |
| 6,159,187 A | 12/2000 | Park et al. |
| 6,162,171 A | 12/2000 | Ng et al. |
| 6,179,776 B1 | 1/2001 | Adams et al. |
| 6,190,357 B1 | 2/2001 | Ferrari et al. |
| 6,217,565 B1 | 4/2001 | Cohen |
| 6,296,644 B1 | 10/2001 | Surat et al. |
| 6,309,346 B1 | 10/2001 | Farhadi |
| 6,352,503 B1 | 3/2002 | Matsu et al. |
| 6,364,878 B1 | 4/2002 | Hall |
| 6,368,315 B1 | 4/2002 | Gillis et al. |
| 6,468,203 B2 | 10/2002 | Belson |
| 6,485,409 B1 | 11/2002 | Voloshin et al. |
| 6,503,225 B1 | 1/2003 | Kirsch et al. |
| 6,517,477 B1 | 2/2003 | Wendlandt |
| 6,547,724 B1 | 4/2003 | Soble et al. |
| 6,572,538 B2 | 6/2003 | Takase |
| 6,572,590 B1 | 6/2003 | Stevens et al. |
| 6,579,277 B1 | 6/2003 | Rabiner et al. |
| 6,610,007 B2 | 8/2003 | Belson et al. |
| 6,612,982 B1 | 9/2003 | Ouchi |
| 6,616,628 B2 | 9/2003 | Hayzelden |
| 6,620,126 B2 | 9/2003 | Unsworth et al. |
| 6,623,424 B2 | 9/2003 | Hayakawa et al. |
| 6,712,832 B2 | 3/2004 | Shah |
| 6,726,677 B1 | 4/2004 | Flaherty et al. |
| 6,730,020 B2 | 5/2004 | Peng et al. |
| 6,780,151 B2 | 8/2004 | Grabover et al. |
| 6,783,491 B2 | 8/2004 | Saadat et al. |
| 6,790,173 B2 | 9/2004 | Saadat et al. |
| 6,793,621 B2 | 9/2004 | Butler et al. |
| 6,793,661 B2 | 9/2004 | Hamilton et al. |
| 6,800,056 B2 | 10/2004 | Tartaglia et al. |
| 6,869,393 B2 | 3/2005 | Butler |
| 6,899,673 B2 | 5/2005 | Ogura et al. |
| 6,911,004 B2 | 6/2005 | Kim et al. |
| 6,923,754 B2 | 8/2005 | Lubock |
| 6,960,162 B2 | 11/2005 | Saadat et al. |
| 6,974,411 B2 | 12/2005 | Belson |
| 6,984,203 B2 | 1/2006 | Tartaglia et al. |
| 7,060,199 B2 | 6/2006 | Woydt et al. |
| 7,172,552 B2 | 2/2007 | Wendlandt |
| 7,214,230 B2 | 5/2007 | Brock et al. |
| 7,273,469 B1 | 9/2007 | Chan et al. |
| 7,288,101 B2 | 10/2007 | Deem et al. |
| 7,291,127 B2 | 11/2007 | Eidenschink |
| 7,365,509 B2 | 4/2008 | Park et al. |
| 7,438,712 B2 | 10/2008 | Chouinard |
| 7,511,733 B2 | 3/2009 | Takizawa et al. |
| 7,537,562 B2 | 5/2009 | Takano |
| 7,559,916 B2 | 7/2009 | Smith et al. |
| 7,591,782 B2 | 9/2009 | Fujikura |
| 7,598,652 B2 | 10/2009 | Kornbluh et al. |
| 7,695,428 B2 | 4/2010 | Machida |
| 7,736,323 B2 | 6/2010 | Von Weymarn-Scharli |
| 7,749,196 B2 | 7/2010 | Osborne et al. |
| 7,837,615 B2 * | 11/2010 | Le .......................... A61B 1/31 600/114 |
| 7,850,725 B2 | 12/2010 | Vardi et al. |
| 7,901,347 B2 | 3/2011 | Sekiguchi et al. |
| 7,909,755 B2 | 3/2011 | Itoi |
| 7,918,819 B2 | 4/2011 | Karmarkar et al. |
| 7,918,845 B2 | 4/2011 | Saadat et al. |
| 7,931,661 B2 | 4/2011 | Saadat et al. |
| 7,935,047 B2 | 5/2011 | Yoshida et al. |
| 7,947,000 B2 | 5/2011 | Vargas et al. |
| 7,957,790 B2 | 6/2011 | Kleen |
| 7,970,455 B2 | 6/2011 | Zilberstein et al. |
| 7,988,621 B2 | 8/2011 | Smith et al. |
| 8,047,236 B2 | 11/2011 | Perry |
| 8,075,476 B2 | 12/2011 | Vargas |
| 8,092,374 B2 | 1/2012 | Smith et al. |
| 8,109,953 B1 | 2/2012 | King, III et al. |
| 8,123,739 B2 | 2/2012 | McQueen et al. |
| 8,125,755 B2 | 2/2012 | Garcia et al. |

(56) References Cited

U.S. PATENT DOCUMENTS

| | | | |
|---|---|---|---|
| 8,192,422 B2 | 6/2012 | Zubiate et al. |
| 8,206,287 B2 | 6/2012 | Matsuo |
| 8,226,548 B2 | 7/2012 | Kucklick |
| 8,241,299 B2 | 8/2012 | Hibner |
| 8,246,575 B2 | 8/2012 | Viola |
| 8,257,257 B2 | 9/2012 | Takizawa et al. |
| 8,298,161 B2 | 10/2012 | Vargas |
| 8,313,014 B2 | 11/2012 | Bettuchi |
| 8,361,090 B2 | 1/2013 | Belson |
| 8,366,606 B2 | 2/2013 | Watanabe et al. |
| 8,388,519 B2 | 3/2013 | Garcia et al. |
| 8,439,825 B2 | 5/2013 | Sekiguchi |
| 8,460,179 B2 | 6/2013 | Ikeda et al. |
| 8,485,968 B2 | 7/2013 | Weimer et al. |
| 8,496,648 B2 | 7/2013 | Rogers |
| 8,506,479 B2 | 8/2013 | Piskun et al. |
| 8,517,923 B2 | 8/2013 | Belson et al. |
| 8,545,491 B2 * | 10/2013 | Abboud | A61M 25/1011 606/22 |
| 8,550,989 B2 | 10/2013 | Dohl et al. |
| 8,556,804 B2 | 10/2013 | Smith et al. |
| 8,663,096 B2 | 3/2014 | Viola |
| 8,663,196 B2 | 3/2014 | Kassab et al. |
| 8,708,894 B2 | 4/2014 | Smith et al. |
| 8,721,530 B2 | 5/2014 | Ohline et al. |
| 8,753,312 B2 | 6/2014 | Bowe et al. |
| 8,777,844 B1 | 7/2014 | Sadanand |
| 8,920,369 B2 | 12/2014 | Salahieh et al. |
| 8,969,639 B2 | 3/2015 | Xu et al. |
| 9,011,318 B2 | 4/2015 | Choset et al. |
| 9,066,655 B2 | 6/2015 | Stefanchik et al. |
| 9,114,228 B2 | 8/2015 | Zook et al. |
| 9,125,653 B2 | 9/2015 | Kovach |
| 9,155,451 B2 | 10/2015 | Smith et al. |
| 9,192,284 B2 | 11/2015 | Hirsch et al. |
| 9,192,288 B2 | 11/2015 | Okaniwa |
| 9,211,140 B2 | 12/2015 | Lauryssen et al. |
| 9,220,398 B2 | 12/2015 | Woodley et al. |
| 9,226,825 B2 | 1/2016 | Starksen et al. |
| 9,241,611 B2 | 1/2016 | Konno |
| 9,254,123 B2 | 2/2016 | Alvarez et al. |
| 9,295,511 B2 | 3/2016 | Smith et al. |
| 9,358,073 B2 | 6/2016 | Piligian et al. |
| 9,364,955 B2 | 6/2016 | Oyola et al. |
| 9,386,910 B2 | 7/2016 | West |
| 9,498,108 B1 | 11/2016 | Lombardi |
| 9,498,198 B2 | 11/2016 | Hu et al. |
| 9,505,125 B2 | 11/2016 | Zubiate et al. |
| 9,585,546 B2 | 3/2017 | Surti et al. |
| 9,610,068 B2 | 4/2017 | Kappel et al. |
| 9,649,473 B2 | 5/2017 | Gregorich et al. |
| 9,763,562 B2 | 9/2017 | Avitsian et al. |
| 9,814,372 B2 | 11/2017 | Smith et al. |
| 9,913,570 B2 | 3/2018 | Kucharski et al. |
| 9,937,324 B2 | 4/2018 | Kim et al. |
| 9,993,142 B2 | 6/2018 | Salman et al. |
| 10,092,291 B2 | 10/2018 | Voegele et al. |
| 10,307,042 B2 | 6/2019 | Lombardi |
| 10,463,495 B2 | 11/2019 | Rogers et al. |
| 11,122,971 B2 | 9/2021 | Tilson et al. |
| 11,135,398 B2 | 10/2021 | Tilson et al. |
| 11,219,351 B2 | 1/2022 | Tilson et al. |
| 11,478,608 B2 | 10/2022 | Tilson et al. |
| 11,554,248 B1 | 1/2023 | Tilson et al. |
| 11,724,065 B2 | 8/2023 | Tilson et al. |
| 11,744,443 B2 | 9/2023 | Lopez et al. |
| 11,793,392 B2 | 10/2023 | Tilson et al. |
| 2001/0041881 A1 | 11/2001 | Sarge et al. |
| 2002/0049423 A1 | 4/2002 | Howell et al. |
| 2002/0107478 A1 | 8/2002 | Wendlandt |
| 2002/0161355 A1 | 10/2002 | Wollschlager |
| 2003/0023259 A1 | 1/2003 | Dubrul et al. |
| 2003/0035048 A1 | 2/2003 | Shipp |
| 2003/0083546 A1 | 5/2003 | Butler et al. |
| 2003/0122374 A1 | 7/2003 | Ouchi et al. |
| 2003/0153866 A1 | 8/2003 | Long et al. |
| 2003/0208220 A1 | 11/2003 | Worley et al. |
| 2003/0216681 A1 | 11/2003 | Zhang et al. |
| 2003/0216691 A1 | 11/2003 | Jacobson |
| 2003/0225379 A1 | 12/2003 | Schaffer et al. |
| 2004/0019252 A1 | 1/2004 | Hirata |
| 2004/0044350 A1 | 3/2004 | Martin et al. |
| 2004/0092960 A1 | 5/2004 | Abrams et al. |
| 2004/0186349 A1 | 9/2004 | Ewers et al. |
| 2004/0186350 A1 | 9/2004 | Brenneman et al. |
| 2004/0242958 A1 | 12/2004 | Fujikawa et al. |
| 2004/0243227 A1 | 12/2004 | Starksen et al. |
| 2004/0260236 A1 | 12/2004 | Manning et al. |
| 2005/0005363 A1 | 1/2005 | Giori et al. |
| 2005/0010237 A1 | 1/2005 | Niazi |
| 2005/0085829 A1 | 4/2005 | Kraemer et al. |
| 2005/0154258 A1 | 7/2005 | Tartaglia et al. |
| 2005/0165275 A1 | 7/2005 | Von Felten et al. |
| 2005/0203340 A1 | 9/2005 | Butler et al. |
| 2005/0272974 A1 | 12/2005 | Iddan |
| 2005/0277966 A1 | 12/2005 | Ewers et al. |
| 2006/0041188 A1 | 2/2006 | Dirusso et al. |
| 2006/0047183 A1 | 3/2006 | Park |
| 2006/0058582 A1 | 3/2006 | Maahs et al. |
| 2006/0129130 A1 | 6/2006 | Tal et al. |
| 2006/0192465 A1 | 8/2006 | Kornbluh et al. |
| 2006/0235457 A1 | 10/2006 | Belson |
| 2006/0235458 A1 | 10/2006 | Belson |
| 2006/0258906 A1 | 11/2006 | Binmoeller |
| 2006/0264707 A1 | 11/2006 | Kinney |
| 2006/0264821 A1 | 11/2006 | Vo et al. |
| 2006/0287666 A1 | 12/2006 | Saadat et al. |
| 2007/0015965 A1 | 1/2007 | Cox et al. |
| 2007/0038025 A1 | 2/2007 | Yoshida |
| 2007/0045504 A1 | 3/2007 | Wollschlager |
| 2007/0088367 A1 | 4/2007 | Von Weymarn-Scharli |
| 2007/0100414 A1 | 5/2007 | Licata et al. |
| 2007/0106302 A1 | 5/2007 | Ortiz |
| 2007/0118015 A1 | 5/2007 | Wendlandt |
| 2007/0156018 A1 | 7/2007 | Krauter et al. |
| 2007/0219411 A1 | 9/2007 | Dejima et al. |
| 2007/0239252 A1 | 10/2007 | Hopkins et al. |
| 2007/0250149 A1 | 10/2007 | Oepen et al. |
| 2007/0255101 A1 | 11/2007 | Bar Or |
| 2007/0260121 A1 | 11/2007 | Bakos et al. |
| 2007/0270648 A1 * | 11/2007 | Smith | A61B 1/31 600/139 |
| 2008/0051635 A1 | 2/2008 | Tanaka et al. |
| 2008/0058722 A1 | 3/2008 | Oepen et al. |
| 2008/0091073 A1 | 4/2008 | Park |
| 2008/0103440 A1 | 5/2008 | Ferren et al. |
| 2008/0139887 A1 | 6/2008 | Fitzpatrick |
| 2008/0172037 A1 | 7/2008 | Huang et al. |
| 2008/0188928 A1 | 8/2008 | Salahieh et al. |
| 2008/0200762 A1 | 8/2008 | Stokes et al. |
| 2008/0214893 A1 | 9/2008 | Tartaglia et al. |
| 2008/0234546 A1 | 9/2008 | Kawano et al. |
| 2008/0242928 A1 | 10/2008 | Kawano et al. |
| 2008/0249362 A1 | 10/2008 | Jiang et al. |
| 2008/0262300 A1 | 10/2008 | Ewers et al. |
| 2008/0275299 A1 | 11/2008 | Park |
| 2009/0023983 A1 | 1/2009 | Stefanchik |
| 2009/0048483 A1 | 2/2009 | Yamamoto |
| 2009/0062611 A1 | 3/2009 | Toyama |
| 2009/0062837 A1 | 3/2009 | Gasche et al. |
| 2009/0112063 A1 | 4/2009 | Bakos et al. |
| 2009/0131752 A1 | 5/2009 | Park |
| 2009/0157068 A1 | 6/2009 | Kallel et al. |
| 2009/0187163 A1 | 7/2009 | Uihlein |
| 2009/0240202 A1 | 9/2009 | Drasler et al. |
| 2009/0259200 A1 | 10/2009 | Lampropoulos et al. |
| 2009/0264704 A1 | 10/2009 | Shtul |
| 2010/0010308 A1 | 1/2010 | Braun et al. |
| 2010/0010437 A1 | 1/2010 | Miles et al. |
| 2010/0016663 A1 | 1/2010 | Maisch et al. |
| 2010/0036363 A1 | 2/2010 | Watanabe et al. |
| 2010/0069712 A1 | 3/2010 | Yamaya |
| 2010/0069716 A1 | 3/2010 | Chin et al. |
| 2010/0076451 A1 | 3/2010 | Zwolinski et al. |

(56) References Cited

U.S. PATENT DOCUMENTS

| | | |
|---|---|---|
| 2010/0087711 A1 | 4/2010 | Edwards |
| 2010/0137686 A1 | 6/2010 | Meron et al. |
| 2010/0145151 A1 | 6/2010 | Fukunaga et al. |
| 2010/0160735 A1 | 6/2010 | Bakos |
| 2010/0204546 A1 | 8/2010 | Hassidov et al. |
| 2010/0268025 A1 | 10/2010 | Belson |
| 2010/0331625 A1 | 12/2010 | Rosemurgy et al. |
| 2010/0331820 A1 | 12/2010 | Prisco et al. |
| 2011/0015729 A1 | 1/2011 | Jimenez et al. |
| 2011/0023888 A1 | 2/2011 | Vazales et al. |
| 2011/0040282 A1 | 2/2011 | Uihlein |
| 2011/0046442 A1 | 2/2011 | Matsushita |
| 2011/0049282 A1 | 3/2011 | Danielsson |
| 2011/0054253 A1 | 3/2011 | Jordá Albiñana et al. |
| 2011/0087070 A1 | 4/2011 | Tilson et al. |
| 2011/0237888 A1 | 9/2011 | Matsushita |
| 2011/0245611 A1 | 10/2011 | Yeh et al. |
| 2011/0282149 A1 | 11/2011 | Vargas et al. |
| 2011/0301414 A1 | 12/2011 | Hotto et al. |
| 2011/0306950 A1 | 12/2011 | Cucin |
| 2011/0319714 A1 | 12/2011 | Roelle et al. |
| 2012/0004676 A1 | 1/2012 | Vargas |
| 2012/0022329 A1 | 1/2012 | Wagh et al. |
| 2012/0041291 A1 | 2/2012 | Ferren et al. |
| 2012/0095548 A1 | 4/2012 | Gregorich et al. |
| 2012/0108902 A1 | 5/2012 | Frassica et al. |
| 2012/0130173 A1 | 5/2012 | Lutze et al. |
| 2012/0143005 A1 | 6/2012 | Yeh et al. |
| 2012/0165607 A1 | 6/2012 | Ashida et al. |
| 2012/0165792 A1 | 6/2012 | Ortiz et al. |
| 2012/0172651 A1 | 7/2012 | Cutrer |
| 2012/0209062 A1 | 8/2012 | Qiao |
| 2012/0277528 A1 | 11/2012 | Qiao |
| 2012/0277729 A1 | 11/2012 | Melsheimer |
| 2013/0131641 A1 | 5/2013 | Jimenez et al. |
| 2013/0190565 A1 | 7/2013 | Gora et al. |
| 2013/0338440 A1 | 12/2013 | Sinai et al. |
| 2014/0005683 A1 | 1/2014 | Stand et al. |
| 2014/0073853 A1 | 3/2014 | Swisher et al. |
| 2014/0081169 A1 | 3/2014 | Gerding et al. |
| 2014/0088459 A1 | 3/2014 | Roush et al. |
| 2014/0142393 A1 | 5/2014 | Piskun et al. |
| 2014/0155702 A1 | 6/2014 | Tilson et al. |
| 2014/0155783 A1 | 6/2014 | Starksen et al. |
| 2014/0188054 A1 | 7/2014 | Ijima et al. |
| 2014/0243873 A1 | 8/2014 | Franklin |
| 2014/0275860 A1 | 9/2014 | Rottenberg et al. |
| 2014/0276601 A1 | 9/2014 | Edward |
| 2014/0276642 A1 | 9/2014 | Cully et al. |
| 2014/0343358 A1 | 11/2014 | Hameed et al. |
| 2014/0371764 A1 | 12/2014 | Oyola et al. |
| 2015/0018616 A1 | 1/2015 | Kumoyama |
| 2015/0038919 A1 | 2/2015 | Bramwell et al. |
| 2015/0073216 A1 | 3/2015 | Papay |
| 2015/0073409 A1 | 3/2015 | Watson et al. |
| 2015/0094656 A1 | 4/2015 | Salahich et al. |
| 2015/0119640 A1 | 4/2015 | Reydel |
| 2015/0126814 A1 | 5/2015 | Mesallum et al. |
| 2015/0133729 A1 | 5/2015 | Reydel |
| 2015/0142013 A1 | 5/2015 | Tanner et al. |
| 2015/0148602 A1 | 5/2015 | Hill et al. |
| 2015/0148606 A1 | 5/2015 | Rottenberg et al. |
| 2015/0164314 A1 | 6/2015 | Peterson |
| 2015/0216589 A1 | 8/2015 | Wittenberger et al. |
| 2015/0342608 A1 | 12/2015 | Hernandez |
| 2015/0369325 A1 | 12/2015 | Bureau et al. |
| 2016/0007832 A1 | 1/2016 | Shimada |
| 2016/0066773 A1 | 3/2016 | Cooper et al. |
| 2016/0096004 A1 | 4/2016 | Gerrans et al. |
| 2016/0129547 A1 | 5/2016 | Duescher et al. |
| 2016/0136393 A1 | 5/2016 | Tsal et al. |
| 2016/0174829 A1 | 6/2016 | Reydel |
| 2016/0198935 A1 | 7/2016 | Choi et al. |
| 2016/0270870 A1 | 9/2016 | Kowshik |
| 2016/0287059 A1 | 10/2016 | Ha et al. |
| 2016/0324412 A1 | 11/2016 | Hassidov et al. |
| 2017/0156567 A1 | 6/2017 | Kaneko |
| 2017/0157363 A1 | 6/2017 | Barrish et al. |
| 2017/0340862 A1 | 11/2017 | Calabrese et al. |
| 2017/0360281 A1 | 12/2017 | Ponsky |
| 2018/0015257 A1 | 1/2018 | Krolik et al. |
| 2018/0043134 A1 | 2/2018 | Alvarez et al. |
| 2018/0064366 A1 | 3/2018 | Sweeney et al. |
| 2018/0132705 A1 | 5/2018 | Higuchi |
| 2018/0184885 A1 | 7/2018 | St. George |
| 2018/0249893 A1 | 9/2018 | Yeung et al. |
| 2018/0263469 A1 | 9/2018 | Okaniwa et al. |
| 2018/0264239 A1 | 9/2018 | Piskun |
| 2018/0289925 A1* | 10/2018 | Palmer ............... A61M 25/0043 |
| 2018/0326197 A1 | 11/2018 | McArthur et al. |
| 2018/0361116 A1 | 12/2018 | Quick et al. |
| 2018/0374603 A1 | 12/2018 | Greenwood |
| 2019/0226447 A1 | 7/2019 | Stecher et al. |
| 2020/0030575 A1 | 1/2020 | Bogusky et al. |
| 2020/0100653 A1* | 4/2020 | Nakamura ......... A61B 1/00078 |
| 2020/0171276 A1 | 6/2020 | Onozuka |
| 2020/0178763 A1 | 6/2020 | Tilson et al. |
| 2020/0315433 A1 | 10/2020 | Axon et al. |
| 2020/0383677 A1 | 12/2020 | Piligian et al. |
| 2021/0000505 A1 | 1/2021 | Lenker et al. |
| 2021/0030260 A1 | 2/2021 | Julian et al. |
| 2021/0045626 A1 | 2/2021 | Hsu et al. |
| 2021/0114507 A1 | 4/2021 | Alexander et al. |
| 2021/0137366 A1 | 5/2021 | Tilson et al. |
| 2022/0000355 A1 | 1/2022 | Tilson et al. |
| 2022/0104690 A1 | 4/2022 | Tilson et al. |
| 2022/0323166 A1 | 10/2022 | Tilson et al. |
| 2023/0210351 A1 | 7/2023 | Scheeff et al. |

FOREIGN PATENT DOCUMENTS

| | | |
|---|---|---|
| CN | 1706349 A | 12/2005 |
| CN | 1732855 A | 2/2006 |
| CN | 1806770 A | 7/2006 |
| CN | 1861011 A | 11/2006 |
| CN | 101119765 A | 2/2008 |
| CN | 101129255 A | 2/2008 |
| CN | 101888872 A | 11/2010 |
| CN | 102137628 A | 7/2011 |
| CN | 201899767 U | 7/2011 |
| CN | 102711585 A | 10/2012 |
| CN | 102872519 A | 1/2013 |
| CN | 103384500 A | 11/2013 |
| CN | 104168860 A | 11/2014 |
| CN | 104287684 B | 3/2016 |
| CN | 105759418 A | 7/2016 |
| CN | 105813536 A | 7/2016 |
| CN | 105832279 A | 8/2016 |
| CN | 106137397 A | 11/2016 |
| CN | 106455929 A | 2/2017 |
| CN | 106488744 A | 3/2017 |
| CN | 106659367 A | 5/2017 |
| CN | 107296584 A | 10/2017 |
| DE | 102005039601 A1 | 2/2007 |
| EP | 401129 A1 | 12/1990 |
| EP | 0941743 A2 | 9/1999 |
| EP | 1662972 A2 | 6/2006 |
| EP | 1695657 A1 | 8/2006 |
| EP | 1487318 B1 | 3/2008 |
| EP | 2016914 A2 | 1/2009 |
| EP | 1499227 B1 | 10/2010 |
| EP | 2258322 A2 | 12/2010 |
| EP | 2364637 A1 | 9/2011 |
| EP | 2368481 A1 | 9/2011 |
| EP | 2368483 A1 | 9/2011 |
| EP | 3256052 A1 | 12/2017 |
| EP | 2604175 B1 | 11/2019 |
| GB | 2482355 A | 10/2010 |
| GB | 2497544 A | 6/2013 |
| JP | H05293077 A | 11/1993 |
| JP | 2002125921 A | 5/2002 |
| JP | 2005152300 A | 6/2005 |
| JP | 2005323778 A | 11/2005 |
| JP | 03965108 B2 | 8/2007 |

(56) References Cited

FOREIGN PATENT DOCUMENTS

| | | | |
|---|---|---|---|
| JP | 2009506839 A | 2/2009 |
| JP | 2009507617 A | 2/2009 |
| JP | 2009061173 A | 3/2009 |
| JP | 2011194126 A | 10/2011 |
| JP | 2013176465 A | 9/2013 |
| JP | 2014124475 A | 7/2014 |
| JP | 2015525609 A | 9/2015 |
| JP | 2018500054 A | 1/2018 |
| JP | 2018514350 A | 6/2018 |
| KR | 10-2015-0131502 A | 11/2015 |
| KR | 20180053852 A | 5/2018 |
| WO | WO97/43941 A1 | 11/1997 |
| WO | WO99/053827 A1 | 10/1999 |
| WO | WO03/013348 A1 | 2/2003 |
| WO | WO2005/110199 A1 | 11/2005 |
| WO | WO2005/110200 A1 | 11/2005 |
| WO | WO2007/035931 A2 | 3/2007 |
| WO | WO2008/041809 A1 | 4/2008 |
| WO | WO2008/122969 A1 | 10/2008 |
| WO | WO2008/122997 A1 | 10/2008 |
| WO | WO2009/154192 A1 | 12/2009 |
| WO | WO2011/018147 A1 | 2/2011 |
| WO | WO2011/018157 A1 | 2/2011 |
| WO | WO2011/148172 A2 | 12/2011 |
| WO | WO2012/054480 A2 | 4/2012 |
| WO | WO2012/080947 A1 | 6/2012 |
| WO | WO2012/122288 A2 | 9/2012 |
| WO | WO2016/034598 A1 | 3/2016 |
| WO | WO2017/041052 A1 | 3/2017 |
| WO | WO2018/035452 A1 | 8/2017 |
| WO | WO2019/054867 A1 | 3/2019 |
| WO | WO2020/018934 A1 | 1/2020 |
| WO | WO2020/214221 A1 | 10/2020 |
| WO | WO2020/237426 A1 | 12/2020 |
| WO | WO2021/202336 A1 | 10/2021 |
| WO | WO2021/242884 A1 | 12/2021 |
| WO | WO2022/051682 A1 | 3/2022 |
| WO | WO2022/159861 A1 | 7/2022 |
| WO | WO2022/192515 A3 | 9/2022 |
| WO | WO2023/122667 A1 | 6/2023 |
| WO | WO2023/122767 A2 | 6/2023 |
| WO | WO2023/133403 A1 | 7/2023 |

OTHER PUBLICATIONS

Entrada® colonic overtube product brochure downloaded from internet http://www.usendoscopy.com/~/media/Files/Documents/Spec-Sheet-International/760358c_entrada_intl_ss_web.pdf Accessed Date: Jun. 5, 2017 (the year of publication is sufficiently earlier than the effective U.S. filing date and any foreign priority date so that the particular month of publication is not in issue) 2009.

Filip et al.; Design, Implementation, and Testing of a miniature self-stabilizing capsule endoscope with wireless image transmission capabilities; Intl. Journal "Information Technologies & Knowledge"; 5(1); downloaded from http://www.foibg.com/ijitk/ijitk-vol05/ijitk05-1-p01.pdf on Jul. 28, 2016; (the year of publication is sufficiently earlier than the effective U.S. filing date and any foreign priority date so that the particular month of publication is not in issue) 2011.

Loeve et al.; Endoscope Shaft-Rigidity Control Mechanism: "Forguide"; IEEE Trans. on Biomed. Eng.; 59(2); pp. 542-551; Feb. 2012.

Loeve et al.; Vacuum packed particles as flexible endoscope guides with controllable rigidity; Granular Matter; 12(6); pp. 543-554; Jun. 24, 2010.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness over tube based on low-melting-point-alloy for endoscopic surgery; J. Med. Devices; 10(2); 8 pages; May 12, 2016.

Gomes et al.; U.S. Appl. No. 18/044,027 entitled "Dynamically rigidizing guiderail and methods of use," filed Mar. 3, 2023.

Tilson et al.; U.S. Appl. No. 18/325,974 entitled "Endscope sheath apparatuses," filed May 30, 2023.

Tilson et al.; U.S. Appl. No. 18/325,979 entitled "Apparatuses and methods for determining if an endscope is contaminated," filed May 30, 2023.

Tilson et al.; U.S. Appl. No. 18/325,990 entitled "Multi-lumen port adapter mainfold devices and methods of use," filed May 30, 2023.

Lopez et al.; U.S. Appl. No. 18/334,555 entitled "Layered walls for rididizing devices," filed Jun. 14, 2023.

Tilson et al.; U.S. Appl. No. 18/343,561 entitled "Nested rigidizing devices," filed Jun. 28, 2023.

Tilson et al.; U.S. Appl. No. 18/262,904 entitled "Large diameter hemostasis valves," filed Jul. 25, 2023.

Bearing Works; PTFE Datasheet; 2 pages; Jan. 21, 2021 retrieved from the Internet (https://www.bearingworks.com/uploaded-assets/pdfs/retainers/ptfe-datasheet.pdf) on Nov. 10, 2023.

Tilson et al.; U.S. Appl. No. 18/235,719 entitled "External working channels," filed Aug. 18, 2023.

Tanner et al.; U.S. Appl. No. 18/550,123 entitled "Control of robotic dynamically rigidizing composite medical structures," filed Sep. 11, 2023.

Mayinger et al.; Disposable-sheath, flexible gastroscope system versus standard gastroscopes: a prospective, randomized trial; Gastrointestinal Endoscopy; 50(4); pp. 461-467; Oct. 1999.

Ofstead et al.; A systematic review of disposable sheath use during flexible endoscopy; Aorn Journal; 109(6); pp. 757-771; Jun. 2019.

Rothstein et al.; Disposable, sheathed, flexible sigmoidoscopy: a prospective, multicenter, randomized trial; Gastrointestinal Endoscopy; 41(6); pp. 566-572; Jun. 1995.

Sardinha et al.; Efficiency and productivity of a sheathed fiberoptic sigmoidoscope compared with a conventional sigmoidoscope; Diseases of the Colon and Rectum; 40(10); pp. 1248-1253; Oct. 1997.

Tilson et al.; U.S. Appl. No. 18/582,634 entitled "Methods of attaching a rigidizing sheath to an endoscope," filed Feb. 20, 2024.

\* cited by examiner (not to scale)

(not to scale)

DEVICES AND METHODS TO PREVENT INADVERTENT MOTION OF DYNAMICALLY RIGIDIZING APPARATUSES

CLAIM OF PRIORITY

This patent application is the U.S. National Stage Entry of International Patent Application No. PCT/US2022/014497, titled "DEVICES AND METHODS TO PREVENT INADVERTENT MOTION OF DYNAMICALLY RIGIDIZING APPARATUSES," filed Jan. 31, 2022, now Publication No. WO 2022/165302 A1, which claims priority to U.S. provisional patent application No. 63/143,739, titled "DEVICES AND METHODS TO PREVENT INADVERTENT MOTION OF DYNAMICALLY RIGIDIZING APPARATUSES," and filed on Jan. 29, 2021, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Devices that can transition on demand between a flexible configuration and a rigid configuration, including, but not limited to devices that can transition between a flexible tubular configuration and a rigid tubular configuration, may be referred to as "dynamically rigidizing" or simply "rigidizing" devices. Such devices have a high clinical utility for a range of conditions. For example, dynamically rigidizing apparatuses can be useful for procedures within anatomical locations that are long and tortuous and for which there is a high end-load applied, for procedures that involves precise sub-anatomy interrogation, and/or for procedures in which time is particularly critical (e.g., during a stroke).

Dynamically rigidizing apparatuses may be placed into the anatomy in a flexible configuration and may then be transitioned to a rigid configuration within the anatomy. A procedure can then be performed within the anatomy while the device is in a rigid configuration. Before rigidizing apparatuses are translated within the anatomy (e.g., for the procedure or for removal upon completion), they are typically transitioned back to the flexible configuration. Translating the device within the anatomy while the device is in the rigid configuration has the potential to cause damage to the patient's anatomy. It would be advantageous to have a rigidizing apparatus (e.g., device, system, etc.) and/or methods of using such apparatuses that mitigates the risks of a rigidizing apparatus being inadvertently translated in the anatomy while in the rigid configuration.

SUMMARY OF THE DISCLOSURE

Described herein are rigidizing apparatuses (e.g., devices and systems, including systems incorporating these devices) and method of using rigidizing apparatuses that limit or prevent the risk of trauma during operation by separating the physical properties of flexibility and stiffness. This enables apparatus to be placed in the anatomy in a flexible state in a manner that reduces the forces applied to the adjacent tissue structures. Once located at the target anatomy, and rigidized, the structure is rigidized along the anatomical pathway minimizing extraneous forces such as spring loading common to single modulus devices. The methods and apparatuses described herein may be used with any rigidizing apparatus (e.g., any apparatus, particularly but not limited to tubular apparatuses) that are configured to transform, on demand, between a rigid and a flexible state (or multiple rigid and/or multiple flexible states).

For example, a rigidizing apparatus may include an elongate flexible tube having a plurality of layers and at least one inlet between the plurality of layers configured to attach to a source of vacuum or pressure. The rigidizing apparatus may be configured to have a rigid configuration when vacuum or pressure is applied through the inlet and a flexible configuration when vacuum or pressure is not applied (or is released).

An advantage of dynamic rigidization is its ability to navigate along and conform to the anatomical pathway. The human circulatory is made of multiple branch vessels and can be tortuous. A dynamically rigidizing pathway allows for the catheter to follow the anatomic pathway in a manner that reduces forces applied to the blood vessels that would ordinarily be required to straighten the pathway and reduce curvature to accommodate a single modulus catheter. Anatomic conformation confers an element of protection and reduces the potential for trauma by more closely following the natural orientation of the blood vessels prior to rigidizing along the pathway.

As described herein, a rigidizing apparatus may include a controller configured to prevent or limit translation of the rigidizing apparatus when the rigidizing apparatus is in the rigid configuration. In particular, described herein are apparatuses including one or more rigidizing members (rigidizing apparatuses) that include a controller configured to determine position (e.g., relative position) and/or rigidizing state (e.g., rigid, semi-rigid, flexible) and/or movement or intended movement (e.g., a robotically controlled instruction to move) and alert (e.g., warn against movement), prevent movement, and/or transform all or some of the apparatus to a flexible configuration to prevent harm to a patient.

Any of the apparatuses described herein may include one or more beacons, fiducials, or other components to enhance visibility and location determination services using a physiological mapping system.

In some examples a rigidizing apparatus includes a flexible tube having a plurality of layers and one or more inlets into a region between the plurality of layers configured to attach to a source of vacuum or pressure. The rigidizing apparatus is configured to have a rigid configuration when vacuum or pressure is applied through the inlet and a flexible configuration when vacuum or pressure is not applied between the plurality of layers. In some examples the rigidizing apparatus may be configured to automatically transition from the rigid configuration to the flexible configuration when the rigidizing apparatus is translated or when a user commands the apparatus to translate in the rigid configuration. Any of these rigidizable members may be elongate rigidizable members (including tubular, cylindrical, etc. rigidizable member). In some examples the rigidizable members may be sheet rigidizable members (that may be shaped in a flexible layer configuration into any shape and converted into a rigid or semi-rigid shape in a rigid configuration).

For example, described herein are apparatuses comprising: a rigidizable member configured to convert between a rigid configuration and a flexible configuration, wherein the flexible configuration is configured to conform to an anatomical region; a sensor configured to detect a force or acceleration indicating movement of the rigidizable member; a controller receiving input from the sensor, wherein the controller is configured to determine when the rigidizable member is in a rigid configuration and when the sensor detects a force or acceleration indicating movement of the rigidizable member that exceeds a threshold value and to trigger a protection response, wherein the protection response is one or more of: emitting an alert, and converting the rigidizable member from the rigid configuration to the flexible configuration or a semi-rigid configuration.

A protection response may prevent movement of the rigid form of the rigidizable member. For example, the apparatuses described herein may be configured to prevent damage to the body preventing (locking, delaying, etc.) translation and/or rotation of the rigidizable member in one or more directions until the rigidizable member has been converted to semi-rigidized or flexible configuration. In some examples the protection response may include automatically converting the rigidizable member to a semi-rigidized or flexible configuration. In some examples the portion response may include alerting a user (emitting a tone, text message, light/visual indicator, etc.) so that the user may convert the rigidizable member to a semi-rigidized or flexible configuration. In some examples the protection response may time out after a predetermined or user-determined time. In some examples the protection response may be overridden by the user.

The rigidizable member may include a plurality of layers and an inlet in fluid communication with the plurality of layers and configured to couple to a source of vacuum or positive pressure. For example, the rigidizable member may be configured to convert between the rigid configuration and the flexible configuration by the application of positive pressure or vacuum.

The sensor may comprise an accelerometer and/or a force sensor. In some examples the sensor is on the rigidizable member. For example, the sensor may be on a handle for the rigidizable member. In some examples the sensor is configured to detect either or both translational movement and rotational movement.

In some examples the sensor comprises a pressure sensor configured to detect pressure within or applied to the rigidizable member, wherein the controller is configured to determine when the rigidizable member is rigid based on the pressure sensor. The controller may be configured to trigger a protection response comprising emitting an audible and/or visible signal. The controller may be configured to trigger a protection response comprising converting the rigidizable member from the rigid configuration to the flexible configuration. The controller may be configured to trigger a protection response comprising locking the position of the rigidizable member.

Any of these apparatuses may include a relief valve in communication with the controller, wherein the controller is configured to open the relief valve as part of the protection response.

The rigidizable member may comprise an overtube, a catheter, a probe, or a sleeve.

For example, described herein are apparatuses comprising: an elongate rigidizable member comprising a plurality of layers, wherein the elongate rigidizable member is configured to convert between a rigid configuration and a flexible configuration by the application of a positive pressure or a negative pressure; a sensor configured to detect a force or acceleration indicating movement of the elongate rigidizable member; a controller receiving input from the sensor, wherein the controller is configured to determine when the rigidizable member is in a rigid configuration and when the sensor detects a force or acceleration indicating movement of the elongate rigidizable member that exceeds a threshold value, and to trigger a protection response comprising releasing the vacuum or positive pressure to convert the rigidizable member from the rigid configuration to the flexible configuration or a semi-rigid configuration. In general, the flexible configuration may be configured to conform to an anatomical region.

Also described herein are methods of operating a rigidizing apparatus having an rigidizing member that is configured to convert between a rigid configuration and a flexible configuration, the method comprising: determining that the rigidizing member is in the rigid configuration; detecting a force or acceleration indicating movement of the rigidizable member; and automatically trigger a protection response, wherein the protection response is one or more of: converting the rigidizable member from the rigid configuration to the flexible configuration or a semi-rigid configuration and emitting an alert.

Determining that the rigidizing member is in the rigid configuration may comprise detecting, in a controller, the pressure within the rigidizing member. In some examples determining that the rigidizing member is in the rigid configuration comprises determining that the pressure within the rigidizing member is above a threshold.

In any of these methods, detecting the force or acceleration may include indicating movement of the rigidizable member comprises detecting a force or acceleration indicating a rotational and/or translational movement.

Any of these methods may include automatically triggering the protection response comprises emitting an audible and/or visible signal. Automatically triggering the protection response may comprise converting the rigidizable member from the rigid configuration to the flexible configuration. In some examples automatically triggering the protection response comprises locking a position of the rigidizable member.

For example, an apparatus may include: an elongate rigidizable member configured to convert between a rigid configuration and a flexible configuration; and a handle coupled to the elongate rigidizable member, wherein at least a portion of the handle is configured to change one or more of: a color, a size and a textual message when the elongate rigidizable member is in the rigid configuration as compared to the at least a portion of the handle when the elongate rigidizable member is in the flexible configuration.

An apparatus may include: an elongate rigidizable member configured to convert between a rigid configuration and a flexible configuration; and a handle coupled to the elongate rigidizable member, wherein the handle is configured to change shape while the elongate rigidizable member is in the rigid configuration relative to the shape of the handle when the rigidizable member is in the flexible configuration. The change in shape of the handle may comprise an enlargement of an overall size of the handle. In any of these examples, the change in shape of the handle may comprise a change in texture of the handle. For example, the handle may be configured to have a sharper texture when the elongate rigidizable member is in the rigid configuration as compared to the texture of the handle when the elongate rigidizable member in the flexible configuration. The change in shape may be caused by a hydraulic pressure.

Any of these apparatuses may include: an elongate rigidizable member configured to convert between a rigid configuration and a flexible configuration; and a handle coupled to the elongate rigidizable member, wherein at least a portion of the handle is configured to change color when the elongate rigidizable member is in the rigid configuration relative to a color of the at least the portion of the handle when the elongate rigidizable member is in the flexible configuration. The handle (or at least a portion of the handle) may be configured to change from a red color when the elongate rigidizable member is in the rigid configuration and a green color when the elongate rigidizable member is in the flexible state. The color change may be deployed by a hydraulic pressure.

Also described herein are apparatus comprising: an elongate rigidizable member configured to convert between a rigid configuration and a flexible configuration; and an audio emitter, wherein the audio emitter is configured to emit an audible noise specific to the rigid configuration when the elongate rigidizable member is in the rigid configuration. The audio emitter may comprise a speaker and/or circuitry configured to generate the sound(s).

For example, the audible noise may be a repeated beep with a regular frequency. The audible noise may include instructions not to move the elongate rigidizable member. The audio emitter may be configured to emit a second audible noise specific to the flexible configuration when the elongate rigidizable member is in the flexible configuration.

In any of the apparatuses described herein a controller (including, for example, control circuitry and/or one or more processors, memory, etc.) may be configured to control the change in shape, size, texture, color, text and/or other indicators indicating that the rigidizable member (e.g., elongate rigidizable member) is rigid and/or not to move the rigidizable member (while in the rigid configuration).

In general, the methods and apparatuses described herein may prevent inadvertent motion, particularly when the apparatus or a rigidizable portion of the apparatus is in a rigid configuration. The apparatuses described herein may generally prevent, limit, or alert the user to movement in one or more directions. Although many of the examples described herein are specific to cylindrical elongate (or tubular) rigidizing members, the methods and apparatuses described herein may be used for any rigidizable member, including planar or sheets of rigidizing members. For example, an apparatus including a rigidizable plate or sheet, motion in the x, y, z directions and/or torques about each in the rigid configuration may be limited or prevented and/or may trigger a protection response. For tubular apparatuses (e.g., tubular rigidizing members), axial motion and/or torsional motion may be specifically limited or prevented, and/or may trigger a protection response.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 1B shows a section through the exemplary vacuum rigidizing member of the apparatus. FIG. 1C shows an enlarged view of a portion of the section, illustrating the arrangement of layers in the un-rigidized configuration.

FIG. 1D shows a longitudinal section through the pressure rigidizing apparatus. FIG. 1E shows a transverse section through the pressure rigidizing apparatus.

DETAILED DESCRIPTION

In general, described herein are rigidizing apparatuses (e.g., rigidizing apparatuses, and systems including one or more rigidizing apparatus, including, but not limited to overtubes, catheters, trocars, endoscopes, etc.) that are configured to prevent harm or damage when rigidized. These apparatuses may be configured as a surgical tool, e.g., to aid in transporting a scope (e.g., endoscope) or other medical instrument through a curved or looped portion of the body (e.g., a vessel). The rigidizing apparatuses can be long, thin, and hollow and can transition relatively quickly between a flexible configuration (i.e., one that is relaxed, limp, or floppy) and a rigid configuration (i.e., one that is stiff and/or holds the shape it is in when it is rigidized). A plurality of layers (e.g., coiled or reinforced layers, slip layers, braided layers, bladder layers and/or sealing sheaths) can together form the wall of the rigidizing apparatuses. The rigidizing apparatuses can transition between the flexible configuration and the rigid configuration, for example, by applying a vacuum or pressure to the wall of the rigidizing apparatus or within the layers forming the wall of the rigidizing apparatus. With the vacuum or positive pressure removed, the layers can easily shear or move relative to each other. With the vacuum or positive pressure applied, the layers can transition to a condition in which they exhibit substantially enhanced ability to resist shear, movement, bending, torque and buckling, thereby providing system rigidization.

The rigidizing apparatuses described herein can provide rigidization for a variety of medical applications, including catheters, sheaths, scopes (e.g., endoscopes), wires, overtubes, trocars or laparoscopic instruments. The rigidizing apparatuses can function as a separate add-on device or can be integrated into the body of catheters, sheaths, scopes, wires, or laparoscopic instruments.

Figure 1A:
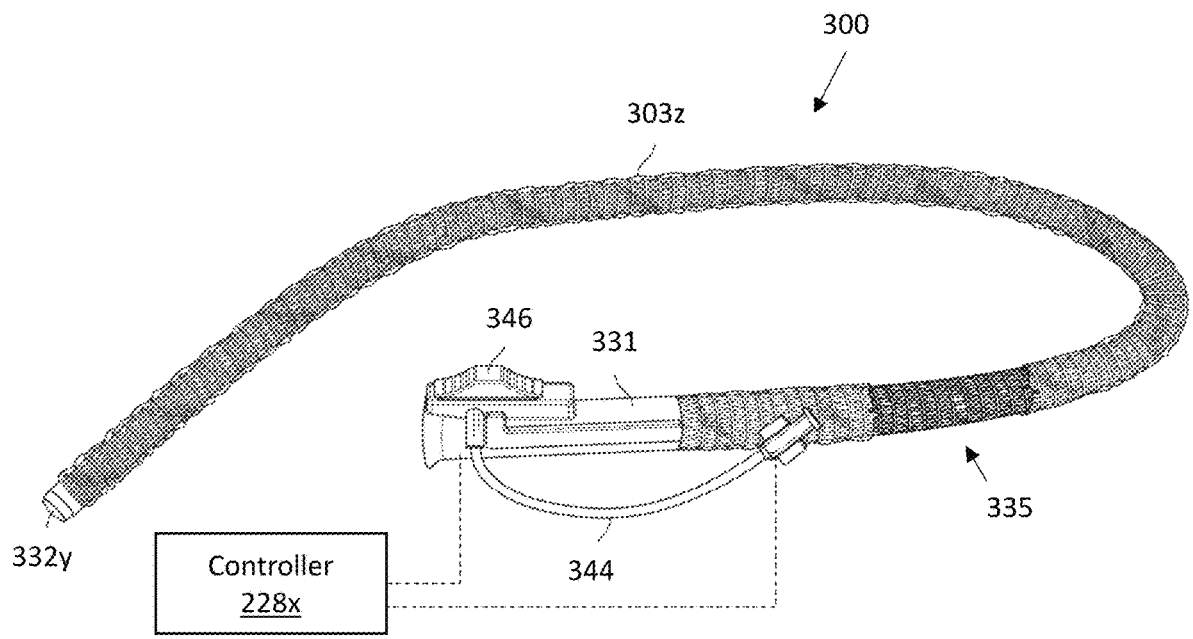
FIG. 1A shows an exemplary rigidizing apparatus.

An example of a rigidizing apparatus 300 is shown in FIG. 1A. The apparatus 300 includes a main rigidizing elongate body 303z having a wall with a plurality of layers including a braid layer, an outer layer (part of which is cut away 335 to show the braid thereunder), and an inner layer. The system further includes a handle 331 having a vacuum or pressure inlet 344 to supply vacuum or pressure to the layers within the rigidizing apparatus 300. An actuator 346 can be used to turn the vacuum or pressure on and off to thereby transition the rigidizing apparatus 300 between flexible and rigid configurations. The distal tip 332y of the rigidizing apparatus 300 can be smooth, flexible, and atraumatic to facilitate distal movement of the main rigidizing elongate body 303z through the anatomy. Further, the tip 332y can taper from the distal end to the proximal end to further facilitate distal movement of the rigidizing apparatus 300 through the anatomy. As will be described in greater detail below any of these apparatuses, including one such as shown in FIG. 1A, may include a controller 228x coupled to the apparatus, including to the rigidizing member (elongate body 303z) and/or the source of positive and/or negative pressure (or a pressure line 344 coupled to the source). The controller may be configured to prevent or limit movement of the portion of the apparatus that is in the rigid configuration, including in particular when this portion of the apparatus is within a patient body.

A rigidizing apparatus, once rigidized, may lock into the shape it is in when the vacuum or pressure is applied; the rigidizing process may be performed without changing the shape of the apparatus during the transition from flexible to rigid, i.e., it does not straighten, bend, or otherwise substantially modify its shape (e.g., it may stiffen in a looped configuration, a serpentine shape, a curve, etc.). The application of positive or negative (e.g., vacuum) pressure between the inner or outer layers (e.g., including the inner coil-wound tube) can be a small percentage (e.g., 5%) of the maximum load capability of the rigidizing apparatus in bending, thereby allowing the rigidizing apparatus to resist straightening. In some examples, upon release of the vacuum or pressure, braids or strands within the layers forming the device can unlock relative to one another and again move so as to allow bending of the rigidizing apparatus. As the rigidizing apparatus is made more flexible through the release of vacuum or pressure it may continue to maintain the shape it was in before the vacuum or pressure was released, i.e., it does not straighten, bend, or otherwise substantially modify its shape. Thus, the rigidizing apparatuses described herein can transition from a flexible, less-stiff configuration to a rigid configuration of higher stiffness by restricting the motion between the strands of braid (e.g., by applying vacuum or pressure).

In some examples, the rigidizing apparatuses described herein are configured to toggle between a rigid configuration and a flexible configuration quickly, and with an indefinite number of transition cycles. In some examples the degree of rigidization (e.g., the stiffness) of the apparatus may also be adjusted, for example, by adjusting the positive pressure (in examples that are rigidized by positive pressure) or vacuum (in examples rigidized by vacuum). As interventional medical devices are made longer and inserted deeper into the human body, and as they are expected to do more exacting therapeutic procedures, there is an increased need for precision and control. Selectively rigidizing apparatuses (including selectively rigidizing overtubes) as described herein can advantageously provide both the benefits of flexibility (when needed) and the benefits of stiffness (when needed). Further, the rigidizing apparatuses described herein can be used, for example, with classic endoscopes, colonoscopes, robotic systems, and/or navigation systems, such as those described in International Patent Application No. PCT/US2016/050290, filed Sep. 2, 2016, titled "DEVICE FOR ENDOSCOPIC ADVANCEMENT THROUGH THE SMALL INTESTINE," the entirety of which is incorporated by referenced herein.

The rigidizing apparatuses described herein can additionally or alternatively include any of the features described with respect to International Patent Application No. PCT/US2016/050290, filed on Sep. 2, 2016, titled "DEVICE FOR ENDOSCOPIC ADVANCEMENT THROUGH THE SMALL INTESTINE," published as WO 2017/041052, International Patent Application No. PCT/US2018/042946, filed on Jul. 19, 2018, titled "DYNAMICALLY RIGIDIZING OVERTUBE," published as WO 2019/018682, International Patent Application No. PCT/US2019/042650, filed on Jul. 19, 2019, titled "DYNAMICALLY RIGIDIZING COMPOSITE MEDICAL STRUCTURES," published as WO 2020/018934, and International Patent Application No. PCT/US2020/013937 filed on Jan. 16, 2020, titled "DYNAMICALLY RIGIDIZING COMPOSITE MEDICAL STRUCTURES," the entireties of which are incorporated by reference herein.

The rigidizing apparatuses described herein can be provided in multiple configurations, including different lengths and diameters. In some examples, the rigidizing apparatuses can include working channels (for instance, for allowing the passage of typical endoscopic tools within the body of the rigidizing apparatus), balloons, nested elements, and/or side-loading features.

For example, a rigidizing apparatus 100 (also referred to as an apparatus, e.g., system and/or device, including a rigidizable member) may be configured to be rigidized by the application of vacuum, e.g., negative pressure. These apparatuses may generally be formed of layers that are configured to form a laminate structure when negative pressure is applied, so that one or more braided or woven layers may be reversibly fused to a flexible outer layer that is driven against a more rigid inner layer without appreciably changing in diameter during pressurization.

Figure 1B:
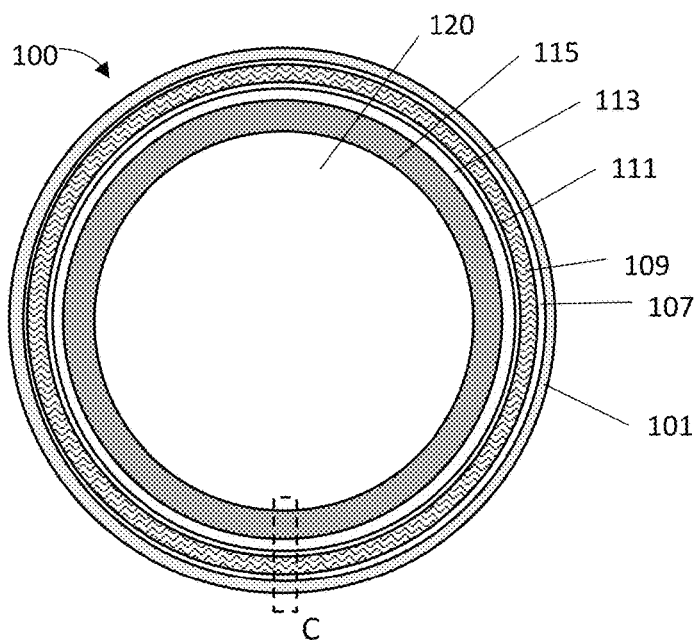
FIGS. 1B and 1C show an example of a portion of a vacuum rigidizing apparatus as described herein.
Figure 1C:
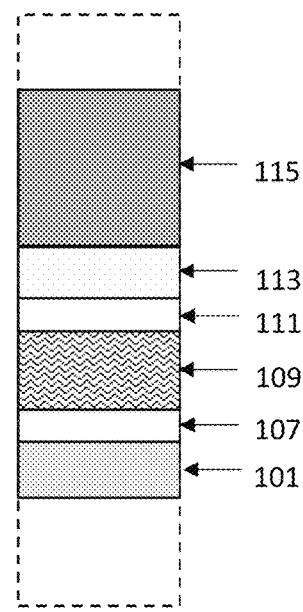

FIGS. 1B-1C illustrate one example of a section through a rigidizing member of an apparatus (e.g., device, system) that is rigidized by the application of vacuum. FIG. 1C shows an enlarged view of an example of an arrangement of the layers of FIG. 1B in the un-rigidized configuration. In this example, the rigidizable member includes an innermost layer 115 that is configured to provide an inner surface against which the remaining layers can be consolidated (e.g., when vacuum is applied). The innermost layer 115 can include a reinforcement element or coil. In particular, the innermost layer 115 may be configured as an inner coil-wound tube (ICWT), e.g., formed of an outer wound wire (e.g., cable, ribbon, wire, etc.) and an inner wound wire arranged on both sides of a layer or tube (e.g., a tie layer). The rigidizing member may also include a slip layer 113 over (e.g., radially outwards of) the innermost layer. The slip layer may be, e.g., a lubrication, coating and/or powder (e.g., talcum powder) on the outer surface of the inner layer 115 and/or within the gap layer 111. A radial gap layer 111 may separate the slip layer 113 from a braid or woven layer 109 (referred to herein for convenience as a "braid layer"), providing a space between the braid layer and the slip layer for the braided layer(s) thereover to move within, e.g., when no vacuum is applied; this space or gap may be removed when vacuum is applied, allowing the braided or woven layer(s) to move radially inward upon application of vacuum. A second gap layer 107 may be present between the braid layer 109 and may be similar to layer 111. Multiple braid layers may be included (e.g., 2, 3 4 or more braid layers may be included) and may be separated by additional gap layers and/or slip layers. The outermost layer 101 can be separated from the braid layer(s) by a gap layer and can be configured to move radially inward when a vacuum is applied to pull down against the braid layer(s) and conform onto the surface(s) thereof. The outermost layer 101 can be soft and atraumatic and can be sealed at both ends to create a vacuum-tight chamber with the innermost layer 115. The outermost layer 101 can be elastomeric, e.g., made of urethane. The hardness of the outermost layer 101 can be, for example, 30 A to 80 A. Further, the outermost layer 101 can have a thickness of 0.0001-0.01", such as approximately 0.001", 0.002, 0.003" or 0.004". Alternatively, the outermost layer can be plastic, including, for example, LDPE, nylon, or PEEK.

Any of these apparatuses may include multiple braid layers; the apparatus may include a tube having a wall formed of a plurality of layers positioned around a lumen 120 (e.g., for placement of an instrument or endoscope therethrough). A vacuum can be supplied between the layers to rigidize the rigidizing apparatus 100. Any of the tubular apparatuses described herein may instead include a solid core forming the inner layer 115.

The innermost layer 115 can be configured to provide an inner surface against which the remaining layers can be consolidated, for example, when a vacuum is applied within the walls of the rigidizing apparatus 100. The structure can be configured to minimize bend force and/or maximize flexibility in the non-vacuum condition.

The layer 109 can be a first braid layer including braided strands. The braid layer can be, for example, 0.001" to 0.040" thick. For example, a braid layer can be 0.001", 0.003", 0.010", 0.015", 0.020", 0.025" or 0.030" thick. In some examples the braid can have tensile or hoop fibers. Hoop fibers can be spiraled and/or woven into a braid layer. Further, the hoop fibers can be positioned at 2-50, e.g., 20-40 hoops per inch. In some examples, the rigidizing apparatuses described herein can have more than one braid layer. For example, the rigidizing apparatuses can include two, three, or four braid layers.

In some examples, the outermost layer 101 can include a lubrication, coating and/or powder (e.g., talcum powder) on the outer surface thereof to improve sliding of the rigidizing apparatus through the anatomy. The coating can be hydrophilic (e.g., a Hydromer® coating or a Surmodics® coating) or hydrophobic (e.g., a fluoropolymer). The coating can be applied, for example, by dipping, painting, or spraying the coating thereon. The innermost layer 115 can similarly include a lubrication, coating (e.g., hydrophilic or hydrophobic coating), and/or powder (e.g., talcum powder) on the inner surface thereof configured to allow the bordering layers to more easily shear relative to each other, particularly when no vacuum is applied to the rigidizing apparatus 100, to maximize flexibility.

A vacuum can be carried within rigidizing apparatus 100 from minimal to full atmospheric vacuum (e.g., approximately 14.7 psi). In some examples, there can be a bleed valve, regulator, or pump control such that vacuum is bled down to any intermediate level to provide a variable stiffness capability. The vacuum pressure can advantageously be used to rigidize the rigidizing apparatus structure by compressing the layer(s) of braided sleeve against neighboring layers. Braid is naturally flexible in bending (i.e. when bent normal to its longitudinal axis), and the lattice structure formed by the interlaced strands distort as the sleeve is bent in order for the braid to conform to the bent shape while resting on the inner layers. This results in lattice geometries where the corner angles of each lattice element change as the braided sleeve bends. When compressed between conformal materials, such as the layers described herein, the lattice elements become locked at their current angles and have enhanced capability to resist deformation upon application of vacuum, thereby rigidizing the entire structure in bending when vacuum is applied. Further, in some examples, the hoop fibers through or over the braid can carry tensile loads that help to prevent local buckling of the braid at high applied bending load. The stiffness of the rigidizing apparatus 100 can increase from 2-fold to over 30-fold, for instance 10-fold, 15-fold, or 20-fold, when transitioned from the flexible configuration to the rigid configuration. In some examples of a vacuum rigidizing apparatus 100, there can be only one braid layer. In other examples of a vacuum rigidizing apparatus 100, there can be two, three, or more braid layers. In some examples, one or more of the radial gap layers or slip layers of rigidizing apparatus 100 can be removed. In some examples, some or all of the slip layers of the rigidizing apparatus 100 can be removed.

The braid layers described herein can act as a variable stiffness layer. The variable stiffness layer can include one or more variable stiffness elements or structures that, when activated (e.g., when vacuum is applied), the bending stiffness and/or shear resistance is increased, resulting in higher rigidity. Other variable stiffness elements can be used in addition to or in place of the braid layer. In some examples, engagers can be used as a variable stiffness element, as described in International Patent Application No. PCT/US2018/042946, filed Jul. 19, 2018, titled "DYNAMICALLY RIGIDIZING OVERTUBE," the entirety of which is incorporated by reference herein. Alternatively or additionally, the variable stiffness element can include particles or granules, jamming layers, scales, rigidizing axial members, rigidizers, longitudinal members or substantially longitudinal members.

The rigidizable apparatuses described herein may also be rigidized by the application of positive pressure, rather than vacuum. For example, referring to FIGS. 1D-1E, the rigidizing apparatus (e.g., device or system) 2100 can be similar to rigidizing apparatus 100 described above, except that it can be configured to hold pressure (e.g., of greater than 1 atm) therein for rigidization rather than vacuum. A pressure-activated rigidizing apparatus 2100 can also include a plurality of layers positioned around a lumen 2120 (e.g., for placement of an instrument or endoscope therethrough).

Figure 1D:
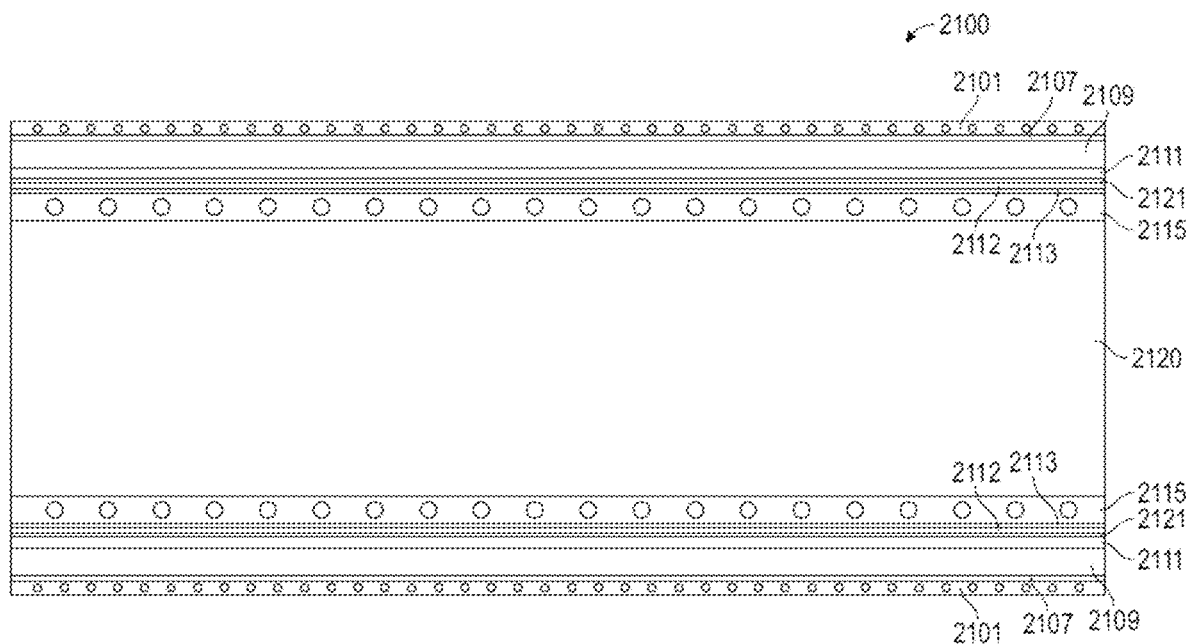
FIGS. 1D-1E show an exemplary pressure rigidizing apparatus.
Figure 1E:
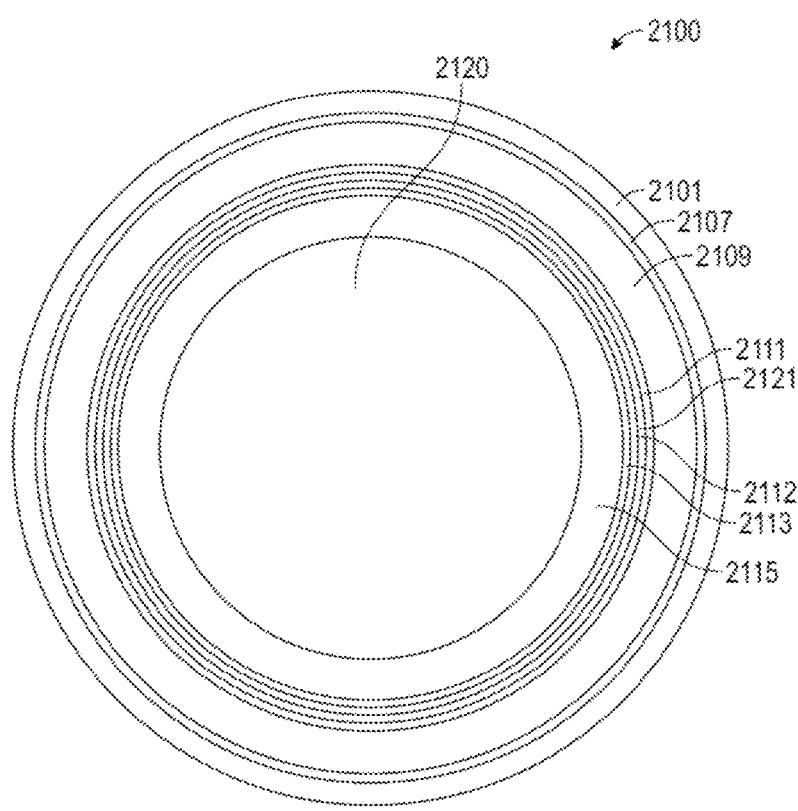

For example, FIGS. 1D-1E illustrate longitudinal and radial sections through an example of a pressure-activated rigidizable member of a rigidizing apparatus. The rigidizing apparatus 2100 shown in FIGS. 1D and 1E can include an innermost layer 2115 (similar to innermost layer 115), which may be an inner coil-wound tube, as described above and in greater detail below. The rigidizing apparatus 2100 may also include a slip layer 2113 (similar to slip layer 113), a pressure gap 2112, a bladder layer 2121, a gap layer 2111 (similar to gap layer 111), a braid layer 2109 (similar to braid layer 109) or other variable stiffness layer as described herein, a gap layer 2107 (similar to layer 107), and an outermost containment layer 2101.

The pressure gap 2112 can be a sealed chamber that provides a gap for the application of pressure to layers of rigidizing apparatus 2100. The pressure can be supplied to the pressure gap 2112 using a fluid or gas inflation/pressure media. The inflation/pressure media can be water or saline or, for example, a lubricating fluid such as oil or glycerin. The lubricating fluid can, for example, help the layers of the rigidizing apparatus 2100 flow over one another in the flexible configuration. The inflation/pressure media can be supplied to the gap 2112 during rigidization of the rigidizing apparatus 2100 and can be partially or fully evacuated therefrom to transform the rigidizing apparatus 2100 back to the flexible configuration. In some examples, the pressure gap 2112 of the rigidizing apparatus 2100 can be connected to a pre-filled pressure source, such as a pre-filled syringe or a pre-filled insufflator, thereby reducing the physician's required set-up time.

The bladder layer (or "bladder") 2121 can be made, for example, of a low durometer elastomer (e.g., of shore 20A to 70A) or a thin plastic sheet. The bladder layer 2121 can be formed out of a thin sheet of plastic or rubber that has been sealed lengthwise to form a tube. The lengthwise seal can be, for instance, a butt or lap joint. For instance, a lap joint can be formed in a lengthwise fashion in a sheet of rubber by melting the rubber at the lap joint or by using an adhesive. In some examples, the bladder layer 2121 can be 0.0002-0.020" thick, such as approximately 0.005" thick. The bladder layer 2121 can be soft, high-friction, stretchy, and/or able to wrinkle easily. In some examples, the bladder layer 2121 is a polyolefin or a PET. The bladder 2121 can be formed, for example, by using methods used to form heat shrink tubing, such as extrusion of a base material and then wall thinning with heat, pressure and/or radiation. When pressure is supplied through the pressure gap 2112, the bladder layer 2121 can expand through the gap layer 2111 to push the braid layer 2109 against the outermost containment layer 2101 such that the relative motion of the braid strands is reduced. Any of the apparatuses descried herein may include multiple filling locations for the bladder and/or a distally located filling location for the bladder layer. Any of the apparatuses described herein may include a bladder that is configured to prevent sticking, e.g., sticking in the closed configuration, as described in greater detail below.

The outermost containment layer 2101 can be a tube, such as an extruded tube. Alternatively, the outermost containment layer 2101 can be a tube in which a reinforcing member (for example, metal wire, including round or rectangular cross-sections) is encapsulated within an elastomeric matrix, similar to as described with respect to the innermost layer for other examples described herein. In some examples, the outermost containment layer 2101 can include a helical spring (e.g., made of circular or flat wire), and/or a tubular braid (such as one made from round or flat metal wire) and a thin elastomeric sheet that is not bonded to the other elements in the layer. The outermost containment layer 2101 can be a tubular structure with a continuous and smooth surface. This can facilitate an outer member that slides against it in close proximity and with locally high contact loads (e.g., a nested configuration as described further herein). Further, the outer layer 2101 can be configured to support compressive loads, such as pinching. Additionally, the outer layer 2101 (e.g., with a reinforcement element therein) can be configured to prevent the rigidizing apparatus 2100 from changing diameter even when pressure is applied.

Because both the outer layer 2101 and the inner layer 2115 may include reinforcement elements therein, the braid layer 2109 can be reasonably constrained from both shrinking diameter (under tensile loads) and growing in diameter (under compression loads).

By using pressure rather than vacuum to transition from the flexible state to the rigid state, the rigidity of the rigidizing apparatus 2100 can be increased. For example, in some examples, the pressure supplied to the pressure gap 2112 can be between 1 and 40 atmospheres, such as between 2 and 40 atmospheres, such as between 4 and 20 atmospheres, such as between and 10 atmospheres. In some examples, the pressure supplied is approximate 2 atm, approximately 4 atmospheres, approximately 5 atmospheres, approximately 10 atmospheres, approximately 20 atmospheres. In some examples, the rigidizing apparatus 2100 can exhibit change in relative bending stiffness (as measured in a simple cantilevered configuration) from the flexible configuration to the rigid configuration of 2-100 times, such as 10-80 times, such as times. For example, the rigidizing apparatus 2100 can have a change in relative bending stiffness from the flexible configuration to the rigid configuration of approximately 10, 15, 20, or 25, 30, 40, 50, or over 100 times.

Figure 2A:
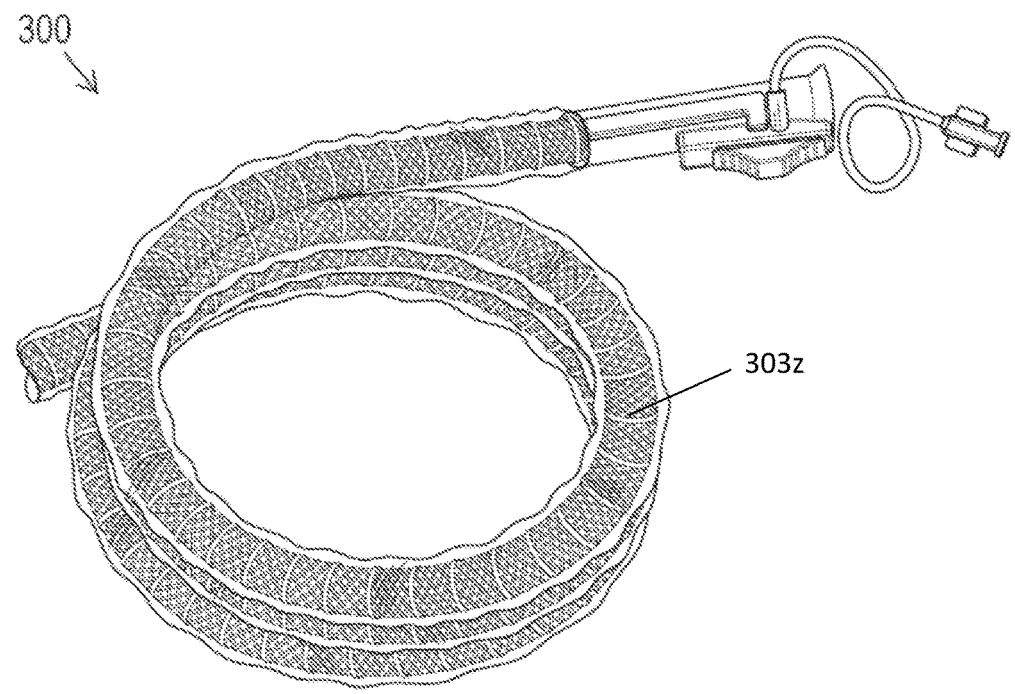
FIGS. 2A and 2B show a rigidizing apparatus in two different exemplary rigidized configurations.
Figure 2B:
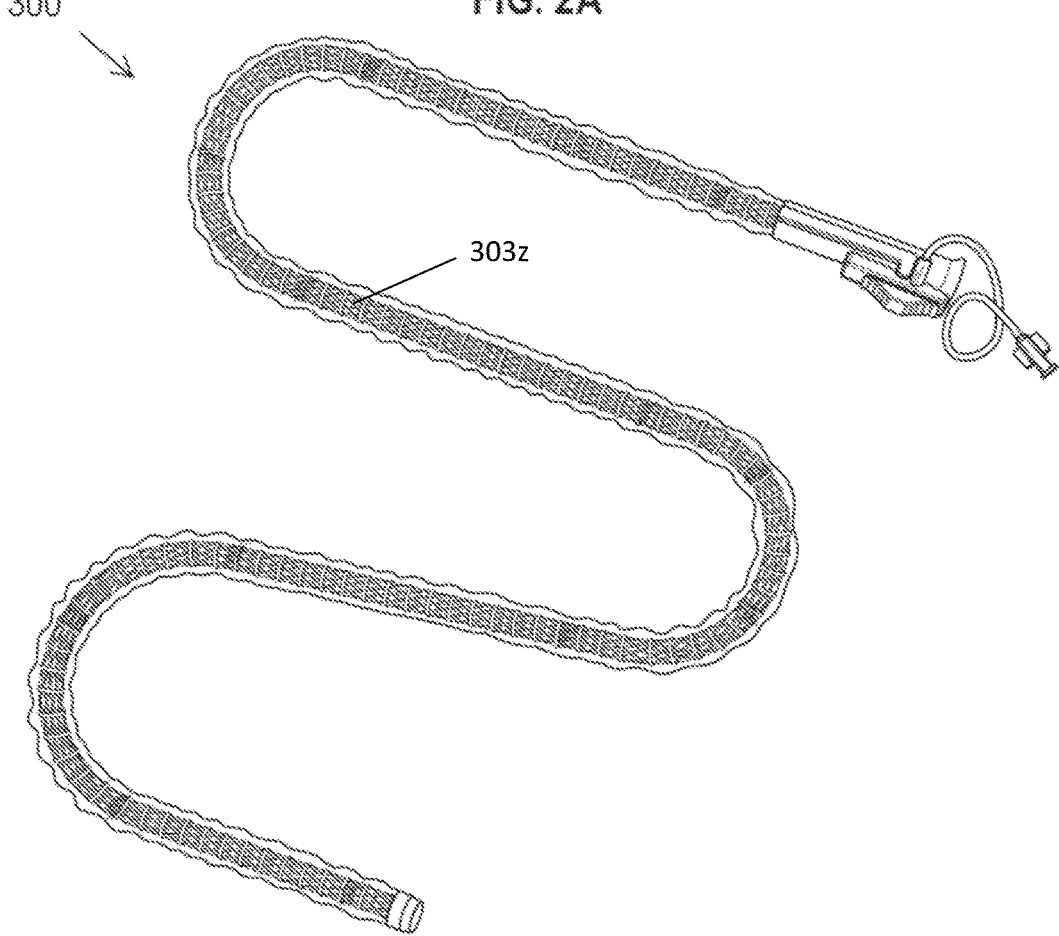

FIGS. 2A and 2B show an example of a rigidizing apparatus 300 in two different rigidized configurations. As the rigidizing member 303z of the rigidizing apparatus 300 is rigidized, it does so in the shape it was in when the vacuum or pressure was applied and does not substantially modify its shape (e.g., it may stiffen in an anatomical conformation, such as a looped configuration as shown in FIG. 2A or in a serpentine shape as shown in FIG. 2B). This can be because the air stiffening effect on the inner or outer layers (e.g., made of coil-wound tube) can be a small percentage (e.g., 5%) of the maximum load capability of the rigidizing apparatus in bending, thereby allowing the rigidizing apparatus to resist straightening. Upon release of the vacuum or pressure, braids or strands can unlock relative to one another and again move so as to allow bending of the rigidizing apparatus. Again, as the rigidizing apparatus 300 is made more flexible through the release of vacuum or pressure, it does so in the shape it was in before the vacuum or pressure was released, i.e., it does not straighten, bend, or otherwise substantially modify its shape and/or remains conformed to the anatomy.

Thus, the rigidizing apparatuses described herein can transition from a flexible, less-stiff configuration to a rigid configuration of higher stiffness by restricting the motion between the strands of braid (e.g., by applying vacuum or pressure).

The rigidizing apparatuses described herein can toggle between the rigid and flexible configurations relatively quickly, and in some examples with an indefinite number of transition cycles. As interventional medical devices are made longer and inserted deeper into the human body, and as they are expected to do more exacting therapeutic procedures, there is an increased need for precision and control (e.g., for a 1:1 transfer of force from the access point to the tip of the device). Selectively rigidizing apparatuses (e.g., overtubes) as described herein can advantageously provide both the benefits of flexibility (when needed) and the benefits of stiffness (when needed). Further, the rigidizing apparatuses described herein can be used, for example, with classic endoscopes, colonoscopes, robotic systems, and/or navigation systems, such as those described in International Patent Application No. PCT/US2016/050290, filed Sep. 2, 2016, titled "DEVICE FOR ENDOSCOPIC ADVANCEMENT THROUGH THE SMALL INTESTINE," the entirety of which is incorporated by referenced herein.

The rigidizing apparatuses described herein can be used, for example, in the gastrointestinal (GI) tract (e.g., the esophagus, stomach, small intestine, and/or colon), in the vasculature (e.g., the neurovasculature, the pulmonary vasculature, and/or the vasculature leading the left or right side of the heart), in urological applications, in gynecological applications, in orthopedics, and/or in the mouth, trachea, lungs, or abdomen.

The rigidizing apparatuses described herein can additionally or alternatively include any of the features described with respect to International Patent Application No. PCT/US2016/050290, filed on Sep. 2, 2016, titled "DEVICE FOR ENDOSCOPIC ADVANCEMENT THROUGH THE SMALL INTESTINE," published as WO 2017/041052, International Patent Application No. PCT/US2018/042946, filed on Jul. 19, 2018, titled "DYNAMICALLY RIGIDIZING OVERTUBE," published as WO 2019/018682, International Patent Application No. PCT/US2019/042650, filed on Jul. 19, 2019, titled "DYNAMICALLY RIGIDIZING COMPOSITE MEDICAL STRUCTURES," published as WO 2020/018934, and International Patent Application No. PCT/US2020/013937 filed on Jan. 16, 2020, titled "DYNAMICALLY RIGIDIZING COMPOSITE MEDICAL STRUCTURES," the entireties of which are incorporated by reference herein.

In some examples, the rigidizing apparatuses described herein can include a mechanism configured to prevent translation (e.g., removal) of the device while the device is in a rigid configuration.

Figure 3:
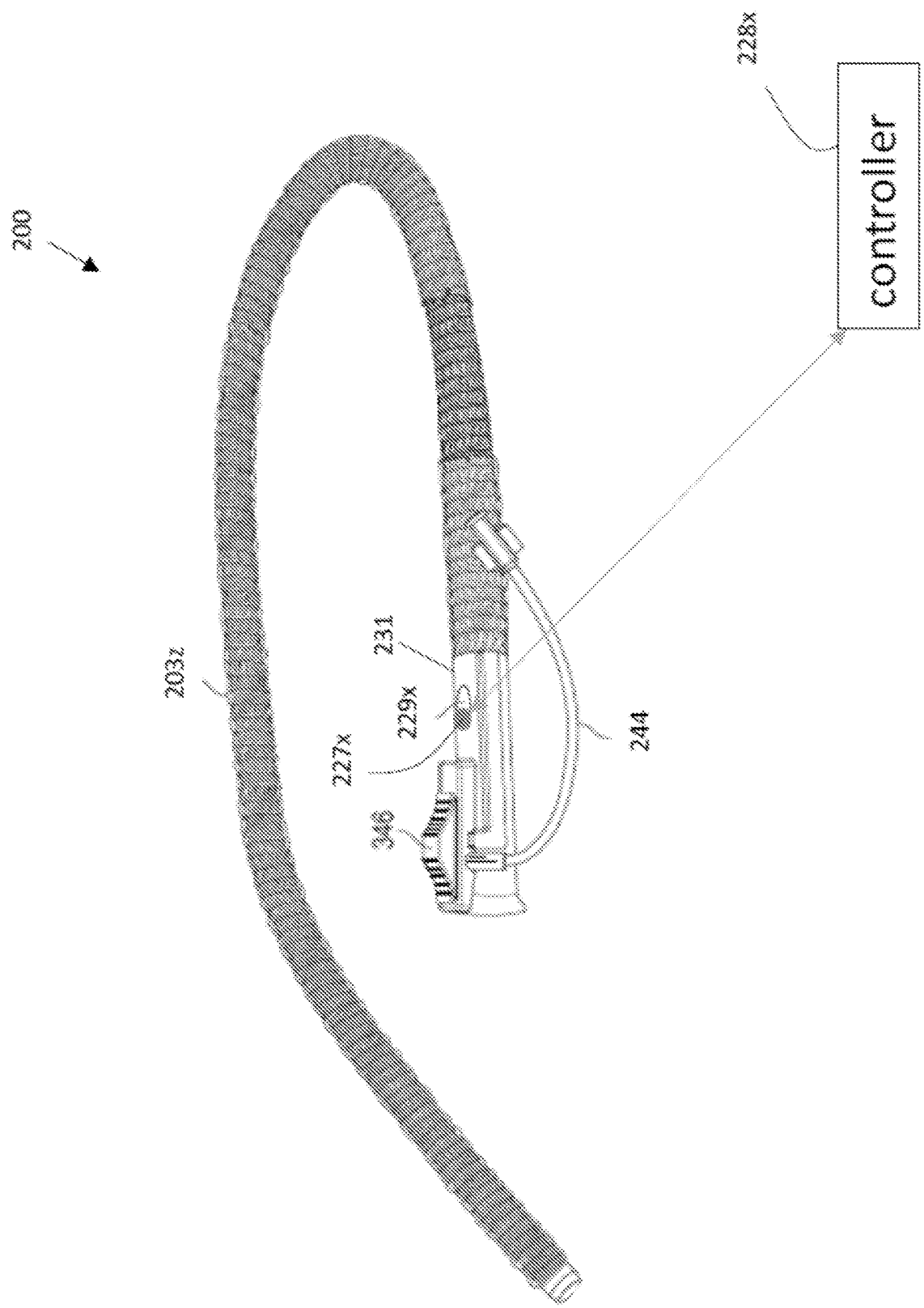
FIG. 3 shows an exemplary rigidizing apparatus configured to prevent unintended translation in the rigidized configuration. The rigidizing apparatus includes a sensor configured to detect movement of the rigidizing apparatus.

Referring to FIG. 3, a rigidizing apparatus 200 can include one or more sensor 227x. In some examples the sensor (as shown in FIG. 3) may be on the handle 231. The sensor 227x can be configured to detect movement of the rigidizing apparatus 200, such as translation, force, and/or acceleration. In some examples, for example, the sensor 227x can be an accelerometer, pressure, force, or gyroscopic sensor. In some examples, the sensor 227x can include or otherwise use MEMS technology. Multiple different sensors may be included and may be positioned in different locations. In some examples the sensor may be positioned on the rigidizable body 203z or within the rigidizable body, including within the wall and/or lumen of the rigidizable body. In some examples, one or more sensors may be positioned at a distal end region of the apparatus.

The sensor 227x can be connected to a controller 228x. The controller may receive process, store and/or transmit sensor data. In particular, the controller may apply control logic using sensor data as well as other data (e.g., pressure/vacuum data, etc.). The controller may include one or more processors. The controller may include a memory, and one or more communications circuits for wired or wireless communication. In some examples the controller includes or is configured to communicate with a relief valve 229x. For example the controller may determine if a motion or force is applied to the rigidizing member 203z above a motion threshold, when the apparatus rigidizing member rigid is sufficiently rigid (e.g., the applied positive or negative pressure and/or the actual measured positive or negative pressure within the rigidizing member exceeds a rigidity threshold), then the controller 228x can open the relief valve 229x to release pressure or vacuum from the main rigidizing elongate body 203z of device 200 and thus transition the main rigidizing elongate body 203z to a flexible configuration. In some examples, the controller 228x can additionally or alternatively trigger an audible warning and/or a visual warning (such as a flashing light), or a tactile warning (such as a vibration). As mentioned above, in some examples, the sensor 227x can be on the main rigidizing elongate body 203z or on the inflation/vacuum line 244 rather than (or in addition to) being on the handle 231.

Figure 4:
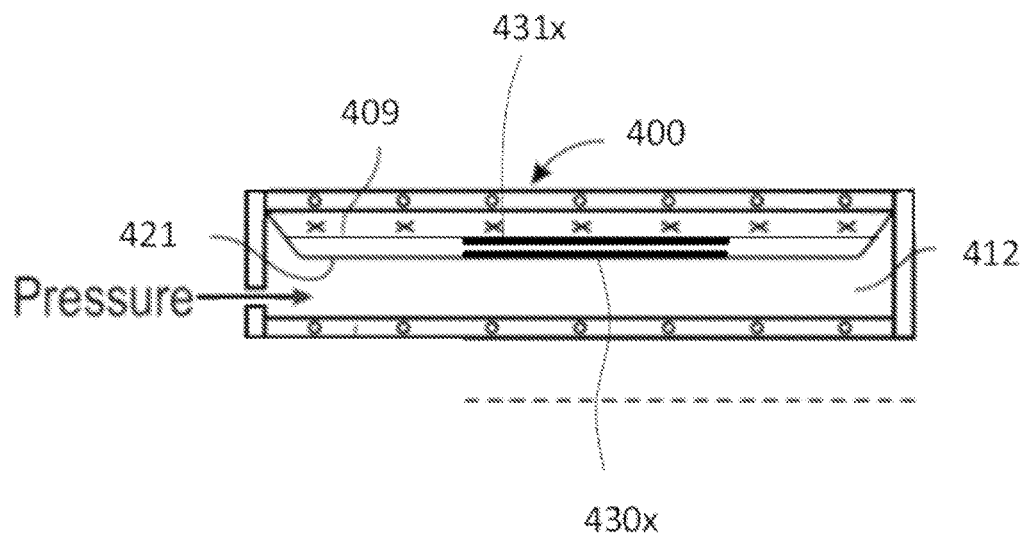
FIG. 4 shows another exemplary rigidizing apparatus configured to prevent unintended translation in the rigidized configuration. The rigidizing apparatus includes first and second segments embedded in the wall configured to contact one another during rigidization.

Any of these apparatuses may include a sensor configured to detect when the rigidifying member is in a sufficiently rigid state. For example, referring to FIG. 4, in some examples, the wall of a rigidizing apparatus 400 can include first and second segments (e.g., strips) 430x, 431x of metal embedded therein. The first segment 430x of metal can be positioned radially inwards of the second segment 431x of metal. An open electrical circuit can extend from the first segment 430x to the second segment 431x. As the rigidizing apparatus 400 is rigidized (e.g., via application of pressure to the pressure gap 412), the bladder 421 can push the first and second segments 430x, 431x together (and against braid layer 409). The contact between the first and second segments 430x, 431x can connect the circuit, triggering an electrical signal to indicate that the device 400 is pressurized and therefore rigidized. The signal can be displayed, for example, on a separate display screen (e.g., fluoroscopy screen or monitor, such as for a computer), on a base station or dock of the device 400, or from a display element on the device 400, such as a light. In some examples, the two segments 430x, 431x can be in the handle (rather than the wall) and configured to contact one another as the actuator on the handle is activated to the on (or rigidized) position. In some examples, the two segments 430x, 431x can be replaced with a pressure sensing device, such as a MEMS silicon pressure sensor, that can detect pressure in the wall and indicate that the device 400 is pressurized.

Figure 5:
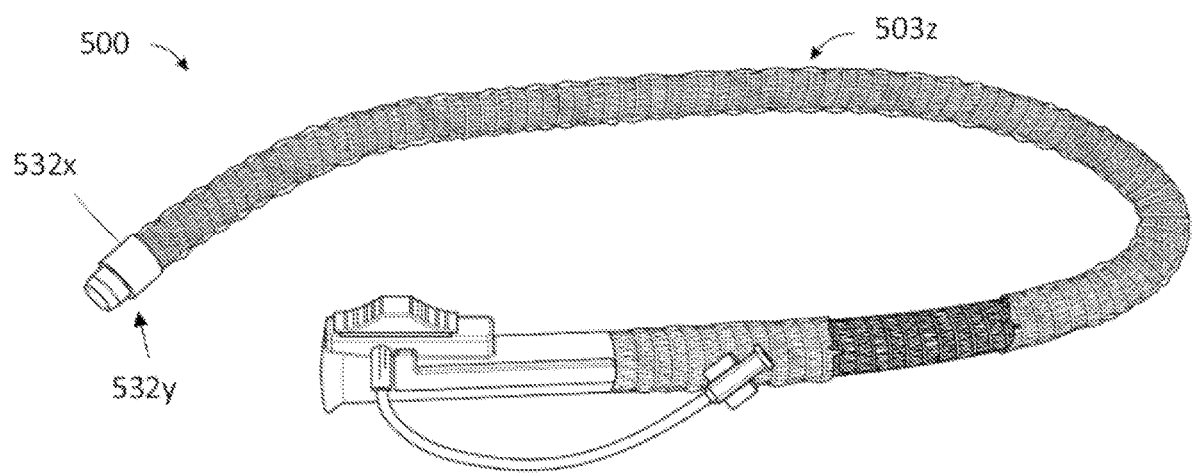
FIG. 5 shows another exemplary rigidizing apparatus configured to prevent unintended translation in the rigidized configuration. The rigidizing apparatus includes a fluoroscopy marker configured to change appearance under fluoroscopy when the device is in a rigid configuration.

The apparatuses described herein may additionally or alternatively include other indicators that the rigidifying member(s) is/are rigid, so as to warn or prevent a user from moving the rigidifying member in the body. For example, referring to FIG. 5, the rigidizing apparatus 500 can include a fluoroscopy marker 532x that changes appearance under fluoroscopy when the main rigidizing elongate body 503z is rigidized. For example, the marker 532x can be a radiopaque element (e.g., annular ring or wire) surrounding and/or embedded proximate to the distal tip 532y of the device 500, which can be closely tracked under fluoroscopy during use. When the device 500 is pressurized, the marker 532x can be squeezed by the wall of the device 500 and can change shape, serving as a fluoroscopic visual indicator of pressurization. In other examples, the marker can be a wire running the length of the main rigidizing elongate body 503z. In other examples, the marker can be on the bladder layer (e.g., can be a radiopaque ink on the bladder). In other examples, the marker can include a radiopaque dye that is used as the pressurization fluid such that, when the device 500 is pressurized, it shows up with enhanced opacity.

Any of these apparatuses may confirm that the rigidifying member of the apparatus includes one or more bends or curves exceeding a threshold before preventing, limiting and/or warning against movement, including longitudinal movement (e.g., inserting/retracting along the long axis of the device). For example any of these apparatuses may include a shape sensor configured to detect or determine the curvature or shape of the elongate rigidizing member. A shape sensor may be, for example a fiber optic shape sensor. If the controller (which may receive and analyze the shape sensor data) determines that the elongate rigidizable member is bent or curved (e.g., greater than a threshold radius of curvature) along its length, it may prevent and/or alert withdrawal and/or advancement of the apparatus in the rigid configuration; linear advancement may be permitted when the elongate rigidizable member is in a linear configuration. The controller may prevent advancement in the rigid configuration by transitioning the apparatus to a flexible (or semi-flexible) configuration, e.g., by releasing pressure (positive or negative pressure) within the elongate rigidizable member.

Any of these apparatuses may be configured to be translated via a robotic means, which may use the same controller or a different controller. In such examples the controller may limit or prevent movement of a rigid elongate rigidizable member when a command for movement (and/or actual movement) is received and/or detected, and the controller may prevent or override the commanded movement instead of, or in addition to transitioning to a flexible or semi-rigid configuration.

In any of these apparatuses the system may allow some movement (within a predefined threshold, but may prevent or limit movement, including by transitioning to a flexible or semi-rigid configuration) beyond the movement threshold. For example, the movement threshold may be an estimated distance movement (e.g., less than 1 mm, less than 2 mm, less than 3 mm, less than 4 mm, less than 5 mm, less than 6 mm, less than 7 mm, less than 8 mm, less than 9 mm, less than 10 mm, etc.), e.g., of the distal end region of the rigidizing member.

In general, any of the movement detection and limiting techniques described herein may be equivalently applied to rotational movements (e.g., rotation of the elongate rigidizable member). The same sensors may be used to determine rotational movement.

Figure 6:
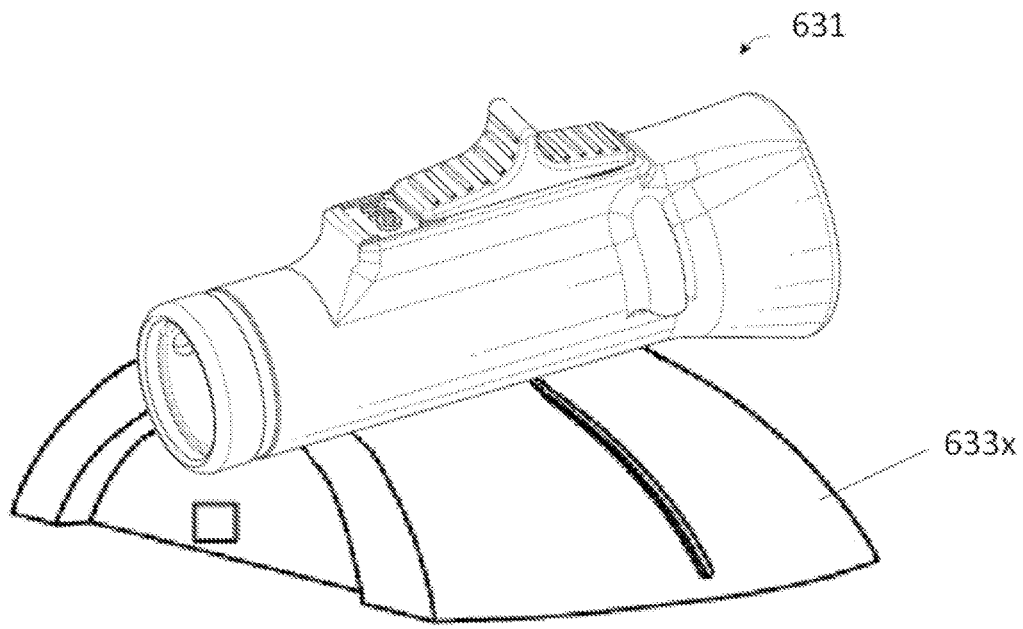
FIG. 6 shows a handle configured to be positioned or locked into a dock to prevent unintended translation of a rigidizing apparatus in the rigidized configuration.

Referring to FIG. 6, in some examples, the handle 631 of a rigidizing apparatus can be configured to be positioned and/or locked onto a dock 633x. To translate the rigidizing apparatus, the user can move the handle 631 from the dock 633x. When the handle 631 is moved from the dock 633x, a pressure relief valve can be triggered and/or a warning activated. In one example, the handle 631 can include a first electrical contact and the dock 633x a second mating electrical contact. A relief valve and/or warning can be actuated when the rigidizing apparatus is moved and the connection between the two contacts is broken. In some examples, the dock 633x can be configured to connect to a surgical drape, surgical bed, or the patient. In some examples, the handle 631 can instead be positioned and/or locked to the drape, surgical bed, or the patient (such that removal therefrom triggers the release of the valve or the warning). In some examples, the handle 631 or rigidizing apparatus can be attached to the dock 633x (or surgical drape, surgical bed, or patient) with an attachment mechanism (e.g., an adhesive strap, a suture, a clip, or a tie) such that removal therefrom triggers the release of the valve or the warning.

Figure 7:
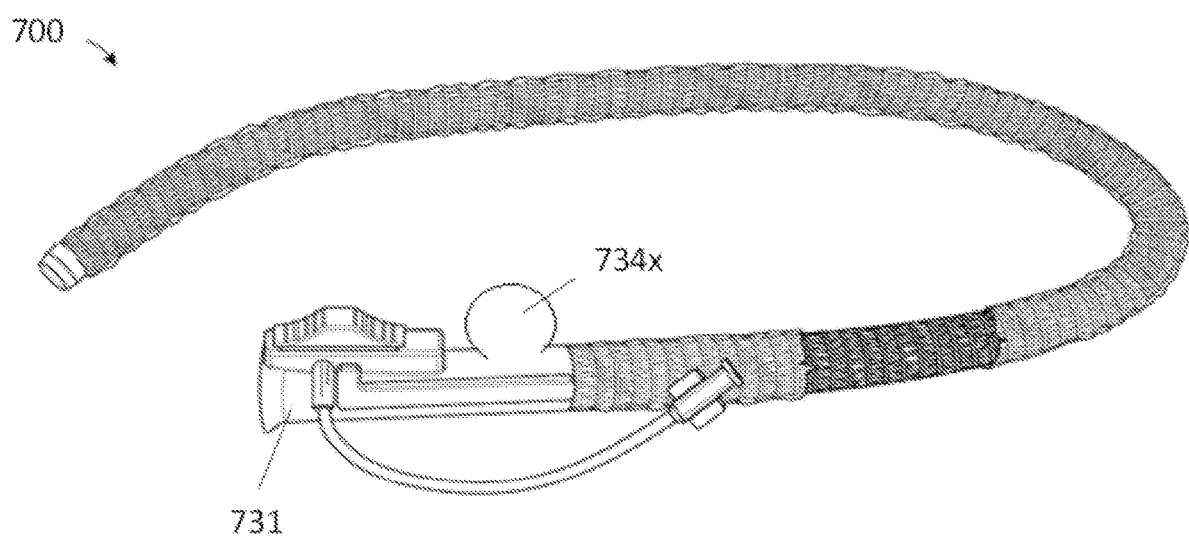
FIG. 7 shows another exemplary rigidizing apparatus configured to prevent unintended translation in the rigidized configuration. The rigidizing apparatus includes a bi-stable indicator.

Referring to FIG. 7, the rigidizing apparatus 700 can include a bi-stable indicator 734x. The bi-stable indicator 734x can serve as a large and prominent visual indicator of the rigidity state of the device 700. For example, as shown in FIG. 7, the bi-stable indicator 734x can be an inflatable element that extends from the handle 731. The bi-stable indicator 734x can additionally or alternatively be an inline inflatable element on the main rigidizing elongate body or the pressure/vacuum input line, a piston that extends from the handle, an airbag or ring that extends around the handle, or an inflatable mechanism that covers gripping features of the handle when pressure is applied. The bi-stable indicator 734x can be actuated via pressure from the input pressure line, electronic signals, and/or a separate hydraulic actuator.

Figure 8:
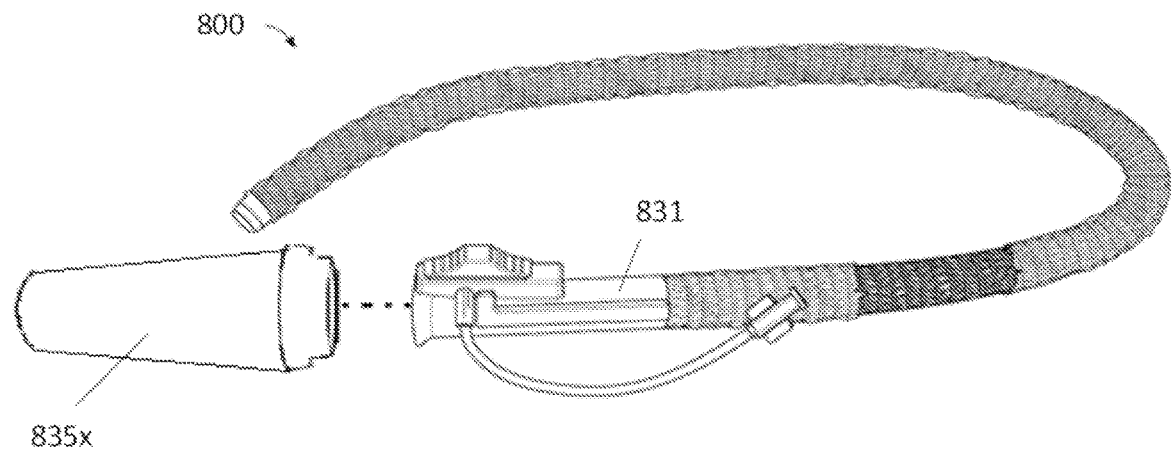
FIG. 8 shows another exemplary rigidizing apparatus configured to prevent unintended translation in the rigidized configuration. The rigidizing apparatus includes a cover configured to be placed over the handle when the device is in the rigidized configuration.

Referring to FIG. 8, in some examples, the rigidizing apparatus 800 can include a handle cover 835x configured to be manually placed over the handle 831 by the user when the device 800 is in the rigid configuration. The user can then be prevented from translating the rigidizing apparatus 800 until the cover 835x has been removed.

Any of these apparatuses, including in particular robotic systems, may include one or more drives for driving movement of the rigidizable member(s), including but not limited to nested rigidizing members. The drive may include a robotic arm or arms, a sled or sleds, or any other actuator for moving the rigidizable member of the apparatus in one or more directions, including rotational and translational (x, y, z) movement. The drive may include a plurality of linkages. The drive may be configured as a rack and pinon structure. The drive may be configured as a linear slide/sled. In some example, the drive and/or controller may include one or more sensors for detecting and controlling movement of the rigidizable member(s) and/or the driver itself.

Figure 9:
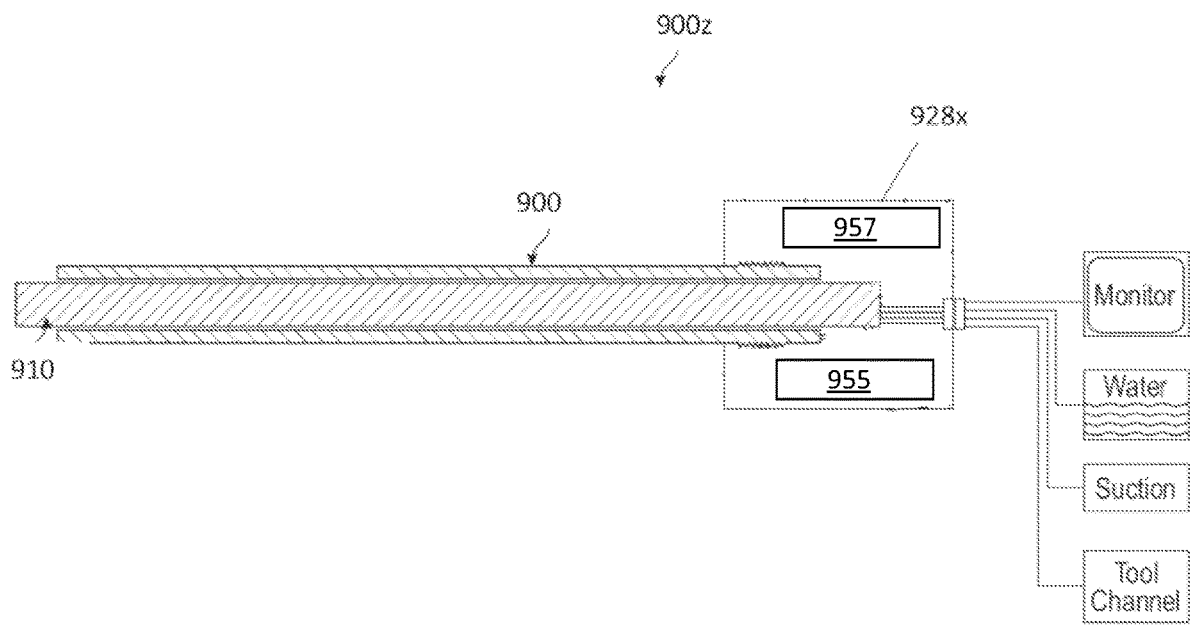
FIG. 9 shows an exemplary rigidizing system including a controller configured to prevent unintended translation in the rigidized configuration.

As mentioned, FIG. 9 shows one example of a schematic of an apparatus including a robotic system. The apparatus includes a pair of nested elongate rigidizable members 900, 910, and a controller 928x. The controller is coupled to a drive 955, as well a source or positive and/or negative pressure 957. Thus controller may coordinate movement and rigidization of the one or more rigidizable members. The same controller, or a separate controller may also coordinate displaying information for the robotic system, including sensor data (e.g., force, shape sensing information, etc.) and/or imaging data (e.g., camera images, models of the anatomy, etc.). The same controller or a separate controller may coordinate the application of fluid and/or suction through the device of a device inserted into a lumen or channel of the apparatus.

Figure 10A:
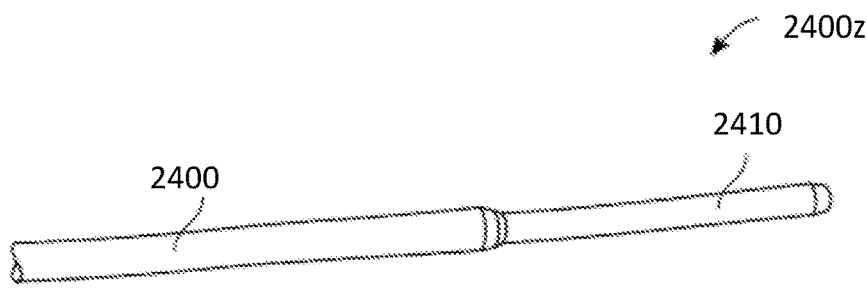
FIGS. 10A-10D illustrate one example of operation of a robotic system including a pair of nested rigidizing members.

FIGS. 10A-10D illustrate one example of an apparatus having a nested set of rigidizable members 2400, 2410. These rigidizable members may include any of the features described herein. In FIG. 10A, the nested system 2400z includes a steerable inner rigidizing member 2410 that is positioned within an outer rigidizing member 2400. The inner rigidizable member 2410 may be driven (axially and/or rotationally) such that the distal end of the inner rigidizing device 2410 extends outside of the outer rigidizing device 2400 and/or retracts into the outer rigidizing device 2400. The apparatus may control (via the controller) in a fully automated manner or in a semi-automatic manner. A user (e.g., doctor, technician, nurse, etc.) may control the movement and positioning of robotic apparatus 2400z by selecting and/or executing pre-defined (e.g., 'macros') of movement and rigidizing states using the pair of nested (e.g. telescoping) rigidizable members.

For example, all or some of the rigidizable members forming the robotic apparatus may be steered. In some examples the distal end regions of each rigidizable members (or in some cases just the inner rigidizable member) may be steered by one or more tendons for pushing, pulling or both pushing and pulling from the proximal end by driver in communication with (or in some examples, integrated into)

the controller. A pressure source (negative and/or positive pressure source) may be integrated into the apparatus.

Figure 10B:
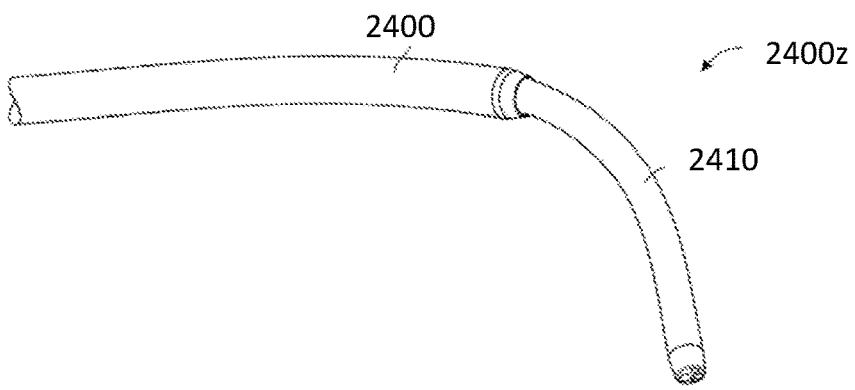
Figure 10C:
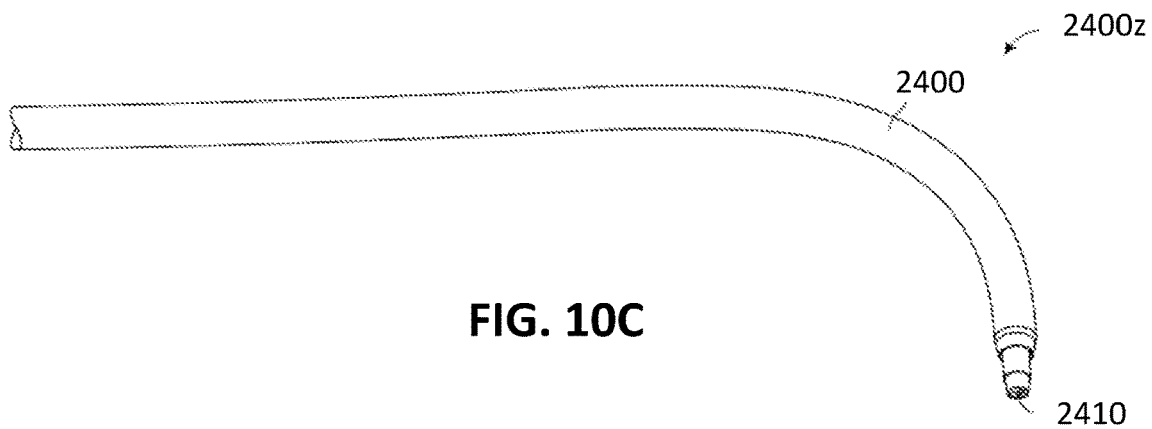
Figure 10D:
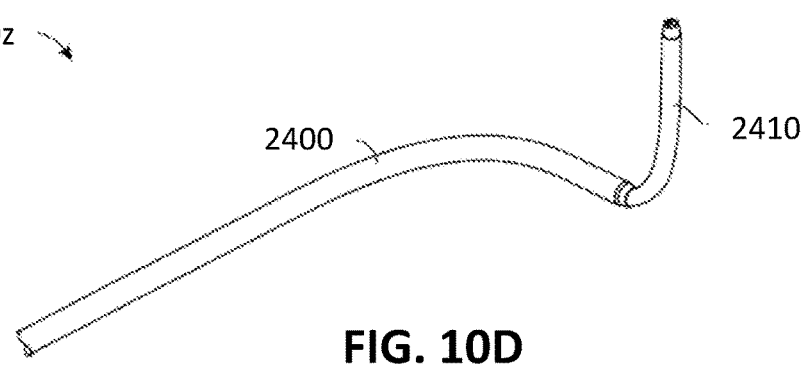

In FIG. 10B, the distal end of the inner rigidizing device 2410 is shown bent in a desired direction/orientation (e.g., via steering cables) and then rigidized (e.g., using vacuum or pressure as described herein). At FIG. 10C, the outer rigidizing device 2400 (in the flexible configuration) is advanced over the rigidized inner rigidizing device 2410 (including over the bending distal section). Once the distal end of the outer rigidizing device 2400 is sufficiently advanced over the distal end of the inner rigidizing device 2410, then the outer rigidizing device 2400 can be rigidized (e.g., using vacuum or pressure as described herein). At FIG. 10D, the inner rigidizing device 2410 can then be transitioned to the flexible state (e.g., by removing the vacuum or pressure as described herein and by allowing the steering cables to go slack such that tip can move easily) and can be advanced and directed/oriented/steered as desired. Alternately, in FIG. 10D, the inner rigidizing device 2410 can be actively steered (either manually or via computational control) as it emerges such that is minimizes the load on the rigidized outer tube. Minimizing the load on the outer rigidizing device 2400 makes it easier for this tube to hold the rigidized shape. Once the inner rigidizing device 2410 is rigidized, the outer rigidizing device 2400 can be transitioned to the flexible state and advanced thereover (as shown in FIG. 10E). The process can then be repeated. The repeated process can result in "shape copying," whereby the inner and outer rigidizing devices 2410, 2400 in the flexible configuration continuously conform to (or copy) the shape of whichever device 2410, 2400 is in the rigid configuration.

In some examples, at the completion of the sequence shown in FIGS. 10A-D, a third rigidizing device can be slid over the first two rigidizing devices (2400, 2410) and rigidized. Rigidizing devices 2400 and 2410 can then be withdrawn. A fourth rigidizing device can be inserted through the inner lumen of the third tube. This fourth rigidizing device may have a larger diameter and more features than rigidizing device 2410. For instance, it may have a larger working channel, more working channels, a better camera, or combinations thereof. This technique can allow two smaller tubes, which tend to be more flexible and maneuverable, to reach deep into the body while still ultimately deliver a larger tube for therapeutic purposes. Alternately, in the example above, the fourth rigidizing device can be a regular endoscope.

In some examples, outer rigidizing device 2400 may be rigidized and then the inner rigidizing device 2410 may be removed. For example, the rigidizing device 2410 may be a "navigation" device comprising a camera, lighting and a distal steering section. The "navigation" device 2410 may be well sealed such that it is easy to clean between procedures. A second inner device may then be placed inside the rigidized outer device 2400 and advanced past the distal end of the outer device 2400. The second inner device may be a "therapeutic" tube comprising such elements as a camera, lights, water, suction and various tools. The "therapeutic" device may not have a steering section or the ability to rigidize, thereby giving additional room in the body of the therapeutic tube for the inclusion of other features, for example, tools for performing therapies. Once in place, the tools on the "therapeutic" tube may be used to perform a therapy in the body, such as, for example, a mucosal resection or dissection in the human GI tract. In another example a third device may be inserted inside inner tube 2410. The third device may be rigidizing and/or an endoscope.

Returning to FIG. 9, FIG. 9 shows an example of a rigidizing system 900z configured as a robotic system including, configured as a nested system with an inner rigidizing apparatus 910 and an outer rigidizing apparatus 900 connected to a controller 928x that is configured to automatically detect motion and immediately vent and/or prevent further movement should the rigidizing system 900z (and/or either of the nested devices 910, 900) be moved. For example, the controller 928x can enable translation of either the inner and/or the outer device 910, 900 only in the flexible configuration (and prevent movement if either the inner or the outer device 910, 900 is rigidized).

In general, any of the apparatuses and methods described herein may be part of and/or configured to be integrated with a robotic system. In particular, the methods and apparatuses described herein may include one or more nested rigidizable members that are configured to be used coaxially with one or more other rigidizable members. Each of the rigidizable members (e.g., "elongate rigidizable members") may be rigidized independently and/or collectively and may be moved independently and/or collectively with the other rigidizable members. The apparatuses described herein may include a controller for coordinating the rigidization and/or movement of the one or more rigidizable members, and/or may adapt a controller for controlling the movement and/or rigidity of the rigidizable members, in addition to controlling other features. Alternatively, multiple controllers may be used. The controller may be in particular electronic controller that are configured to electronically control the movement and rigidization of the rigidizable members, based on user input (e.g., command input) from an input source having multiple inputs (e.g., virtual or actual buttons, dials, sliders, joysticks, etc.).

If it desired to translate both the inner and outer devices 910, 900 together (forward or backwards), such as for withdrawal of the device, then the controller 928x can confirm that both the inner and the outer devices 910, 900 are in the flexible configuration. Whether the inner or outer devices 910, 900 are in the flexible (or rigid) configuration can be determined by both the commanded (i.e., user set) state of the system 900z and also a separate (and redundant) prevention mechanism, such as one of the mechanisms described in the examples of FIGS. 3-8. These systems, including with a singular tube or with a nested tube system, could be used with either manual tools or with tools that are robotically controlled. In some examples, including but not limited to robotically controlled apparatuses, the apparatus may be configured (e.g., by including software, firmware and/or hardware) configured to prevent translation of the apparatus (e.g., the rigidizable member of the apparatus) when in the rigidized state.

In some examples, the rigidizing apparatuses described herein can include a constant audible or visual indicator when the device is in the rigid configuration.

In some examples, the rigidizing apparatuses described herein can additionally or alternatively include a mechanism configured to detect when a user has touched the handle (e.g., when the user intends to translate the rigidizing apparatus). For example, the handle can include a conductive surface electrode configured to detect a change in impedance or conduction when the user touches the handle (e.g., via low power RF energy or capacitance). If the device is in a rigid configuration when the user's touch is detected, a control system connected to the handle can then trigger a signal/warning or transition the device to a flexible configuration as described herein.

In some examples, the rigidizing apparatuses described herein can additionally or alternatively have a mechanism configured to ensure that the insufflator reading does not provide a false sense of flexibility (i.e., to avoid the insufflator pressure suggesting that the rigidizing apparatus is in the flexible configuration when it is actually in the rigid configuration). For example, the rigidizing apparatuses can include a pressure gage mounted directly to the device (e.g., onto the handle). As another example, insufflation can be built directly into and/or connected directly to the handle. The controller may also or alternatively receive data from the pressure gauge.

Although described herein as rigidizing via the application of pressure or vacuum to braid layers, it should be understood that other dynamically rigidizing techniques are possible. For example, the rigidizing apparatuses described herein may rigidize via phase change materials, EAP, granules, cables with links, links with linkages, jamming layers, electrostatic charge, nitinol, and/or magnets and the use of magnetic fields.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

Figure 11A:
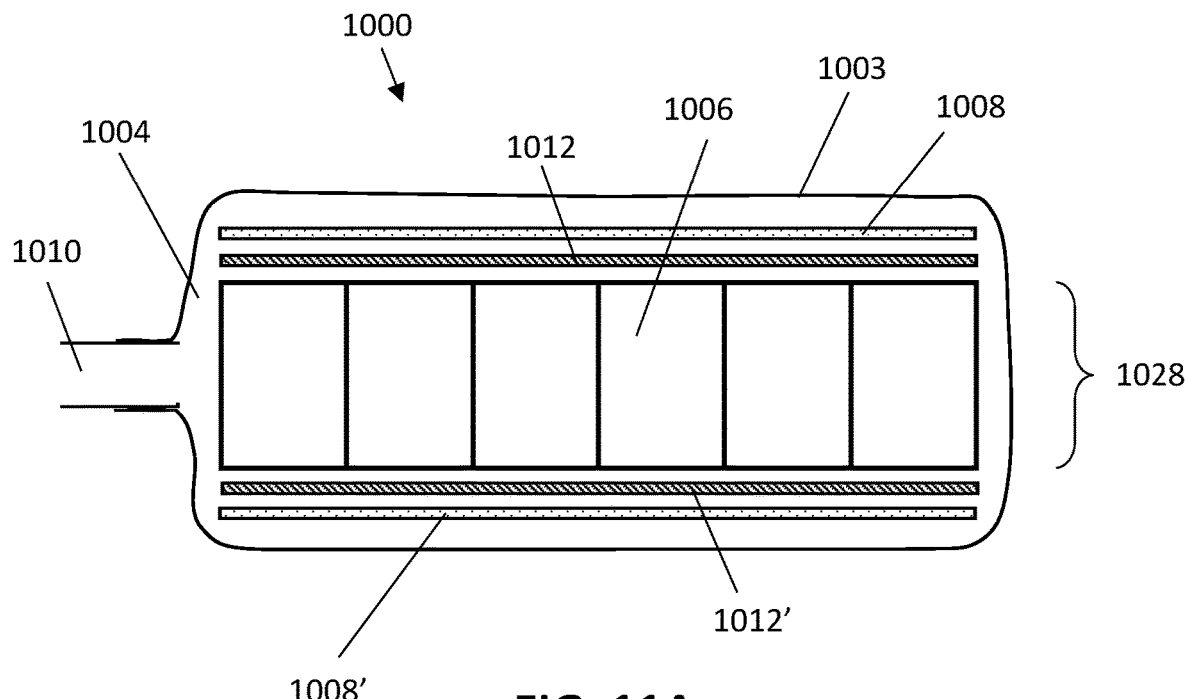
FIGS. 11A-11B schematically illustrates a cross-section through one example of a rigidizable member configured as a reconfigurable shell structure having relaxed (un-rigidized, highly flexible) configuration as shown in FIG. 11A and a rigidized (rigid) configuration as shown in FIG. 11B.
Figure 11B:
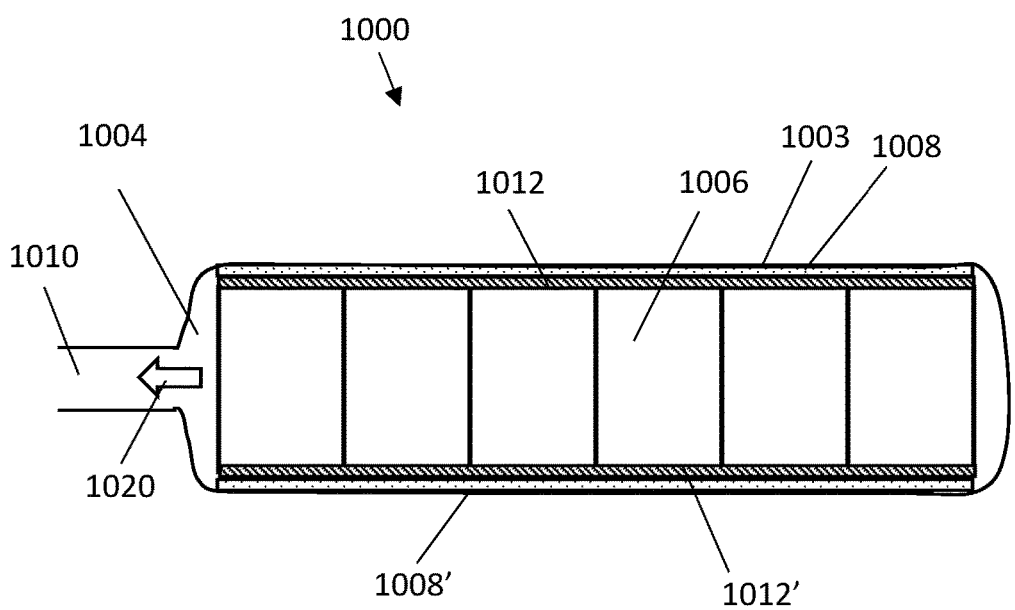

As mentioned above, any of the methods and apparatuses described herein may be used with a rigidizing member that is configured as a rigidizing sheet that is configured to convert between a rigid configuration and a flexible configuration. Thus, the rigidizing members described herein are not limited to elongate, e.g., tubular or cylindrical, rigidizing members, but may include rigidizable structures that may have a flexible sheet configuration that may be rigidized. For example, FIGS. 11A-11B illustrate an example of a cross-sectional schematic view of a rigidizable member configured as a planar reconfigurable structure 1000. In this example (not shown to scale), the structure 1000 comprises a sealed enclosed region 1004. The sealed enclosed region 1004 encloses a single core 1006 that is flanked on the upper surface and the lower surface by inner-fiber shear stabilizing layers 1012, 1012' that are adjacent to outer face sheet layers 1008, 1008'. The enclosed region may be enclosed by, e.g., an elastomeric or plastic material 1003, and may be referred to as the outer sealing container. A vacuum and/or pressure line 1010 is fluidly connected to the sealed region 1004. The vacuum and/or pressure line may be supported to prevent collapse when positive or negative pressure is applied. In some examples the negative pressure (suction) is applied from the end of the apparatus, as shown. Alternatively or additionally, pressure may be distributed within the structure and may be applied at more than one location, and/or at a central location.

FIG. 11B schematically illustrates the apparatus of claim 11A in a rigidized configuration in which negative pressure (vacuum) is applied. In this example the negative pressure laminates the outer face sheets 1008, 1008' against the inter-fiber shear stabilization sheets 1012, 1012' and the core layer 1006. The core may be relatively incompressible in that axis. The spacing between layers in FIG. 11A is exaggerated, as the layers (including the outer sealing chamber) may lay flat, though loosely, against each other in the un-rigidized configuration.

In some examples the rigidizing member may be a reconfigurable structure that encloses a single core that is flanked on the upper surface and the lower surface by inner-fiber shear stabilizing layers that are adjacent to outer face sheet layers. Additional (e.g., a third and fourth) shear stabilizing layers may also be included outside of the outer face sheet layers. In any of the apparatuses described the additional shear stabilizing layers may be present on both sides of the face sheet. This may provide enhanced shear properties with the face sheet, thereby providing enhanced rigidization.

In any of the apparatuses described herein the shear stabilizing layer could be bonded to core (or to respective cores). This may still provide shear enhancing properties relative to the face sheets. It may be more firmly attached and provide enhanced rigidization, while still allowing the core to have flexibility, because the shear stabilizing layers could be an elastomer. Any of the apparatuses described herein may include (e.g., between the inside of the outer sealing container, e.g., bag 1003, and the outer layer of the composite stack of layers, e.g., the outer face sheet 1008 or an outer shear layer), a breathable material, such as a cloth or a random orientation fibered 'breather', that may enhance air evacuation from the apparatus.

As mentioned, the core layer may provide a well-defined thickness or cross-sectional height to the reconfigurable structure, while also providing flexibility. In some embodiments, the core layer comprises a material that is discontinuous along its surface. Discontinuity can refer to the material comprising scores along its surface. Discontinuity can also refer to a material configured, at least in part, as a mesh, web, or net, or otherwise comprising connected strands of material (e.g., honeycomb).

In some embodiments, the core layer comprises a contact area percentage of about 5-100%, 10-100%, 15-100%, 20-100%, 25-100%, 30-100%, 35-100%, 40-100%, 45-100%, 50-100%, 55-100%, 60-100%, 65-100%, 70-100%, 75-100%, 80-100%, 85-100%, 90-100%, 10-90%, 20-80%, 30-70%, 40-60%, 45-55%, etc. In some examples the core contact area may be low (e.g., less than 15%, less than 10%, less than 8%, less than 7%, less than 6%, less than 5%, less than 4%, less than 3%, less than 2%, less than 1%, etc.)

In some embodiments, each core layer comprises a thickness of about 0.1-10 cm, 0.5-10 cm, 0.1-5 cm, 0.5-5 cm, 0.5-2 cm, 1-5 cm, 1-10 cm, 2-10 cm, 2-8 cm, 2-5 cm, 3-10 cm, 3-8 cm, 3-5 cm, 4-10 cm, 4-8 cm, 4-5 cm, 5-10 cm, etc. Multiple core layers may be used and may be separated by shear stabilization layer(s). The overall core thickness may be large. For example, the overall core (or core region) may have a thickness that is between 0.1 cm and 50 cm (e.g., between 0.1 cm and 40 cm, between 1 cm and 35 cm, between 1 cm and 31 cm, between 1 cm and 25 cm, between 1 cm and 16 cm, etc.).

Figure 11C:
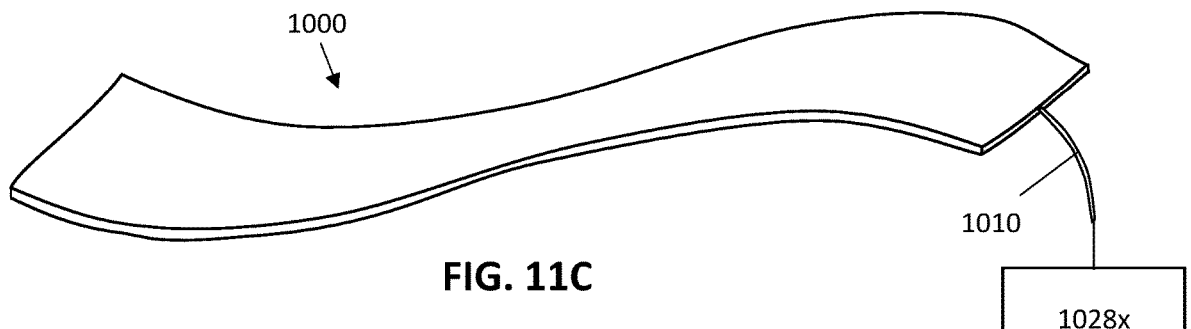
FIGS. 11C-11E illustrate the rigidizable member of FIG. 11A-11B transforming from a flexible configuration (FIGS. 11C and 11D) to a rigid configuration (FIG. 11E) to reversibly assume a shape.
Figure 11D:
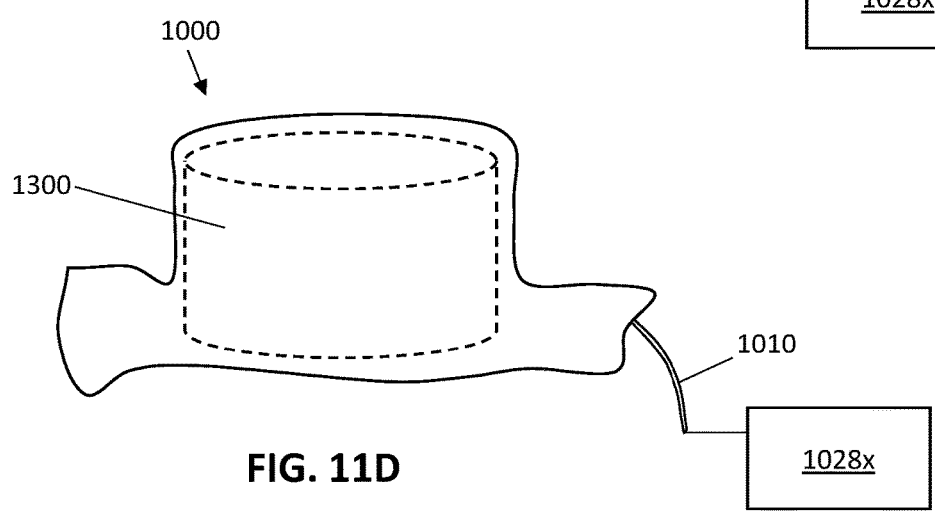
Figure 11E:
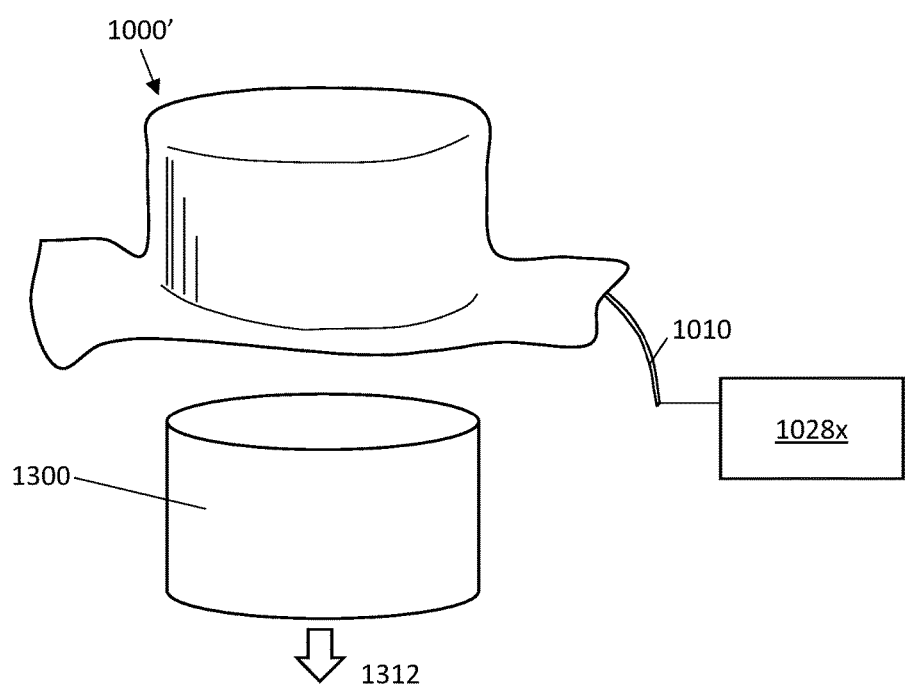

FIGS. 11C-11E illustrate a rigidizing member configured as a sheet of rigidizing member 1000 that is configured to convert between a rigid configuration and a flexible configuration, and that is configured as described herein to prevent or limit moving of the rigidizing member when the rigidizing member is in the rigid configuration. For example, the apparatus may include one or more sensors configured to detect a force or acceleration indicating movement of the rigidizable member, and may include a controller 1028$x$ receiving input from the sensor, wherein the controller is configured to determine when the rigidizable member is in a rigid configuration and when the sensor detects a force or acceleration indicating movement of the rigidizable member that exceeds a threshold value and to trigger a protection response, wherein the protection response is one or more of:

emitting an alert, and converting the rigidizable member from the rigid configuration to the flexible configuration or a semi-rigid configuration.

For example, FIG. 11C shows the rigidizing member 1000 in the flexible (non-rigidized) configuration, forming a flexible and conformable sheet of material that may be easily maneuvered to form a shape before rigidizing the rigidizing member. For example, in FIG. 11D the flexible sheet forming the rigidizing member 1000 is placed over an end of a cylindrical structure 1300 and allowed to conform thereto. Pressure (e.g., negative pressure) may be applied and controlled by a controller 1028x, so that the rigidizing member rigidizes 1000' in the shape of the cylinder 1300, as shown in FIG. 11E. In this configuration the controller may also be configured to detect movement or force applied to the rigidized member 1000', as described above. In FIG. 11E the cylinder may be removed 1312 from under the rigidizing member, but the rigidizing member may be otherwise configured to prevent it from being moved. In some cases the apparatus or method may be configured to allow the rigid rigidized member to be moved in a particular defined path, such as to withdraw or remove the rigid rigidizable member from over a structure or from out of the body, where the one or more sensors and/or a user can detect a structure is not going to interfere with the rigidizing member in the rigid configuration. In some examples the controller may release pressure (converting the rigidizing member from a rigid to a flexible, or semi-rigid stage).

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An apparatus comprising:
    a rigidizable member configured to convert between a rigid configuration and a flexible configuration;
    a first sensor at a proximal end region of the rigidizable member, wherein the first sensor is configured to detect a force or acceleration indicating longitudinal and/or rotational movement of the rigidizable member;
    a pressure sensor configured to detect pressure within the rigidizable member;
    a controller receiving input from the first sensor and the pressure sensor, wherein the controller is configured to trigger a protection response when the rigidizable member is both in a rigid configuration based on the pressure sensor and when the first sensor detects the force or acceleration indicating longitudinal and/or rotational movement of the rigidizable member that exceeds a threshold value, wherein the protection response is one or more of: emitting an alert, locking the position of the rigidizable member, and converting the rigidizable member from the rigid configuration to the flexible configuration or a semi-rigid configuration.

2. The apparatus of claim 1, wherein the rigidizable member comprises a plurality of layers and an inlet in fluid communication with the plurality of layers and configured to couple to a source of vacuum or positive pressure.

3. The apparatus of claim 1, wherein the rigidizable member is configured to convert between the rigid configuration and the flexible configuration by the application of positive pressure or vacuum.

4. The apparatus of claim 1, wherein the first sensor comprises an accelerometer.

5. The apparatus of claim 1, wherein the first sensor comprises a force sensor.

6. The apparatus of claim 1, wherein the first sensor is configured to detect both translational movement and rotational movement.

7. The apparatus of claim 1, wherein the pressure sensor is configured to detect positive or negative pressure within or applied to the rigidizable member.

8. The apparatus of claim 1, wherein the controller is configured to trigger the protection response comprising emitting an audible and/or visible signal.

9. The apparatus of claim 1, wherein the controller is configured to trigger the protection response comprising converting the rigidizable member from the rigid configuration to the flexible configuration.

10. The apparatus of claim 1, wherein the controller is configured to trigger the protection response comprising locking the position of the rigidizable member.

11. The apparatus of claim 1, further comprising a relief valve in communication with the controller, wherein the controller is configured to open the relief valve as part of the protection response.

12. The apparatus of claim 1, wherein the rigidizable member comprises an overtube.

13. An apparatus comprising:
    a rigidizable member configured to convert between a rigid configuration and a flexible configuration;
    a handle region at a proximal end of the rigidizable member;
    a first sensor on the proximal handle region that is configured to detect a force or acceleration indicating longitudinal and/or rotational movement of the rigidizable member;
    a pressure sensor configured to detect when the rigidizable member is rigid based on a pressure within the rigidizable member;
    a controller receiving input from the first sensor and the pressure sensor, wherein the controller is configured to trigger a protection response when the rigidizable member is both in a rigid configuration and when the first sensor detects the force or acceleration indicating longitudinal and/or rotational movement of the rigidizable member from the proximal handle that exceeds a threshold value wherein the protection response is one or more of: emitting an alert, locking the position of the rigidizable member, and converting the rigidizable member from the rigid configuration to the flexible configuration or a semi-rigid configuration.

14. An apparatus comprising: a rigidizable member configured to convert between a rigid configuration and a flexible configuration by a change of pressure;
    a handle region at a proximal end of the rigidizable member;
    a first sensor on the handle region that is configured to detect a force or acceleration indicating longitudinal and/or rotational movement of the rigidizable member;
    a pressure sensor configured to detect pressure within the rigidizable member;
    a controller receiving input from the first sensor and the pressure sensor, wherein the controller is configured to determine when the rigidizable member is rigid based on the detected pressure and to trigger a protection response when the rigidizable member is both in a rigid configuration and when the first sensor detects the force or acceleration indicating longitudinal and/or rotational movement of the rigidizable member from the handle that exceeds a threshold value.

* * * * *